United States Patent
Hazra et al.

(10) Patent No.: US 11,851,464 B2
(45) Date of Patent: Dec. 26, 2023

(54) METHODS AND COMPOSITIONS RELATED TO RECOMBINANT NEIL2

(71) Applicant: Board of Regents, The University of Texas System, Austin, TX (US)

(72) Inventors: Tapas Hazra, Galveston, TX (US); Sanjiv Sur, Galveston, TX (US); Ashok Chopra, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/717,313

(22) Filed: Apr. 11, 2022

(65) Prior Publication Data

US 2022/0259274 A1 Aug. 18, 2022

Related U.S. Application Data

(62) Division of application No. 16/585,271, filed on Sep. 27, 2019, now abandoned.

(60) Provisional application No. 62/738,605, filed on Sep. 28, 2018.

(51) Int. Cl.
| | |
|---|---|
| *C07K 14/47* | (2006.01) |
| *A61P 11/00* | (2006.01) |
| *C12N 15/85* | (2006.01) |
| *A61P 31/04* | (2006.01) |

(52) U.S. Cl.
CPC ............. *C07K 14/47* (2013.01); *A61P 11/00* (2018.01); *A61P 31/04* (2018.01); *C12N 15/85* (2013.01); *C07K 2319/01* (2013.01); *C12N 2015/8518* (2013.01)

(58) Field of Classification Search
CPC ..... C07K 14/47; C07K 2319/01; A61P 11/00; A61P 31/04; C12N 15/85; C12N 2015/8518
See application file for complete search history.

(56) References Cited

U.S. PATENT DOCUMENTS

| | | |
|---|---|---|
| 2010/0119528 A1 | 5/2010 | Sarkar et al. |
| 2011/0110908 A1 | 5/2011 | Wilson et al. |

OTHER PUBLICATIONS

Singh RK et al. Protein Engineering Approaches in the Post-Genomic Era. 2017. Current Protein and Peptide. 18, 1-11. (Year: 2017).*
Zhang M et al. Propagated Perturbations from a Peripheral Mutation Show Interactions Supporting WW Domain Thermostability. 2018. Structure. 26, 1474-1485. (Year: 2018).*
Wu et al. Analysis of the bacterial community in chronic obstructive pulmonary disease sputum samples by denaturing gradient gel electrophoresis and real-time PCR. 2014. BMC Pulmonary Medicine. 14:179. p. 1-7 (Year: 2014).*
Grochowalska et al. Analysis of Acinetobacter baumannii resistance patterns in patients with chronic obstructive pulmonary disease (COPD) in terms of choice of effective empiric antibiotic therapy. 2017. vol. 24, No. 2. p. 307-311 (Year: 2017).*
Genbank Q969S2.3. Genbank 2017. p. 1-7. (Year: 2017).*
Ba, et al., "8-Oxoguanine DNA Glycosylase-1 Augments Proinflammatory Gene Expression by Facilitating the Recruitment of Site-Specific Transcription Factors," Journal of Immunology, 192(5):2384-2394, 2014.
Bhakat, et al., "Acetylation of the Human DNA Glycosylase NEIL2 and Inhibition of Its Activity," Nucleic Acids Research, 32(10):3033-3039, 2004.
Chakraborty, et al. "Neil2-Null Mice Accumulate Oxidized DNA Bases in the Transcriptionally Active Sequences of the Genome and Are Susceptible to Innate Inflammation," The Journal of Biological Chemistry, 290(41): 24636-24648, 2015.
Das, et al., "A Critical Role for NF-Kappa B in GATA3 Expression and TH2 Differentiation in Allergic Airway Inflammation," Nature Immunology, 2(1):45-50, 2001.
Fleming, et al., "Oxidative DNA Damage is Epigenetic by Regulating Gene Transcription Via Base Excision Repair," PNAS, 114(10):2604-2609, 2017.
Hazra, et al., "Identification and Characterization of a Novel Human DNA Glycosylase for Repair of Cytosine-Derived Lesions," Journal of Biological Chemistry, 277(34): 30417-30420, 2002.
Hosoki, et al., "Facilitation of Allergic Sensitization and Allergic Airway Inflammation by Pollen-Induced Innate Neutrophil Recruitment," American Journal of Respiratory Cell and Molecular Biology, 54(1): 81-90, 2016.
Hosoki, et al., "Innate Mechanism of Pollen- and Cat Dander-Induced Oxidative Stress and DNA Damage in the Airways," The Journal of Allergy and Clinical Immunology, 140(5): 1436-1439, 2017.
Hosoki, et al., "Myeloid Differentiation Protein 2 Facilitates Pollen- and Cat Dander-Induced Innate and Allergic Airway Inflammation," The Journal of Allergy and Clinical Immunology; 137(5):1506-1513, e2), 2016.
Hosoki, et al., "Neutrophil Recruitment by Allergens Contribute to Allergic Sensitization and Allergic Inflammation," Current Opinion in Allergy and Clinical Immunology, 16(1): 45-50, 2016.
Huang, et al., "Lipid-Based Signaling Modulates DNA Repair Response and Survival Against Klebsiella Pneumoniae Infection in Host Cells and In Mice," Am J Respir Cell Mal Biol, 49: 798-807, 2013.
Kaplan, et al., Stat6 is Required for Mediating Responses to IL-4 and for the Development of Th2 Cells, Immunity, 4 (3):313-319, 1996.
Sarkar, et al., "Peptide Carrier-Mediated Non-Covalent Delivery of Unmodified Cisplatin, Methotrexate and Other Agents via Intravenous Route to the Brain," PLoS One,, 9(5): e97655, 2014.
Takeda, et al., "Essential Role of Stat6 in IL-4 Signaling," Nature, 380(6575): 627-630, 1996.

(Continued)

*Primary Examiner* — Paul J Holland

(57) ABSTRACT

Certain embodiments are directed to NEIL2 compositions and method of using NEIL2 composition to treat subjects in need of such treatment.

7 Claims, 13 Drawing Sheets

Specification includes a Sequence Listing.

(56) References Cited

OTHER PUBLICATIONS

Tiner, et al., "Combinational Deletion of Three Membrane Protein-Encoding Genes Highly Attenuates Yersinia Pestis While Retaining Immunogenicity in a Mouse Model of Pneumonic Plague," Infection and Immunity, 83(4): 1318-1338, 2015.
Tiner, et al., "Immunisation of Two Rodent Species with New Live-Attenuated Mutants of Yersinia Pestis CO92 Induces Protective Long-Term Humoral- and Cell-Mediated Immunity Against Pneumonic Plague," NPJ Vaccines, 1:16020, 2016.
Tiner, et al., "Intramuscular Immunization of Mice with a Live-Attenuated Triple Mutant Yersinia Pestis CO92 Induces Robust Humoral and Cell-Mediated Immunity to Completely Protect Animals Against Pneumonic Plague," Clinical and Vaccine Immunology, 22: 1255-1268, 2015.
Yang, et al., "Essential Role of Nuclear Factor kb in the Induction of Eosinophilia in Allergic Airway Inflammation," The Journal of Experimental Medicine, 188(9): 1739-1750, 1998.

\* cited by examiner

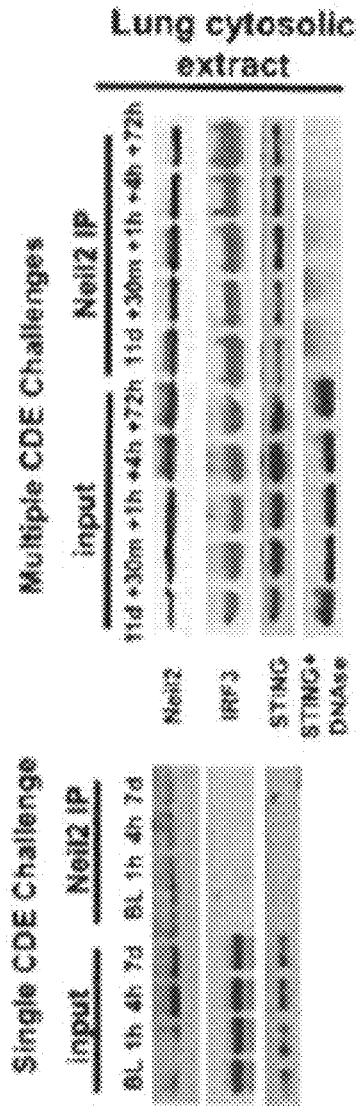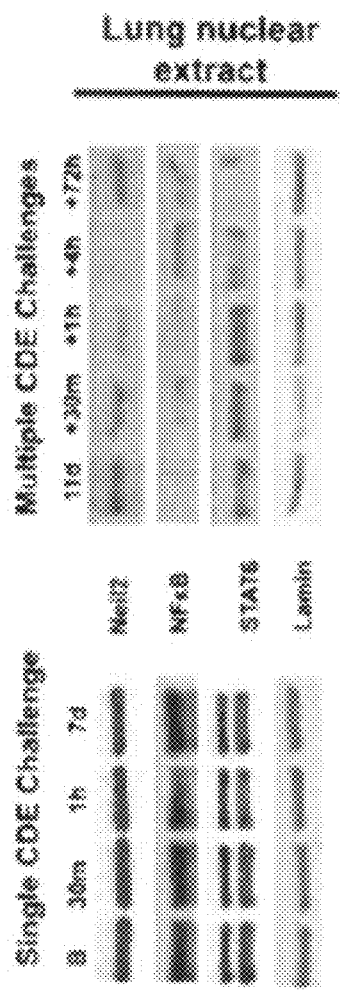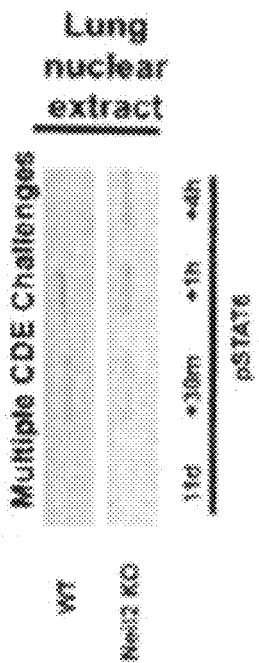

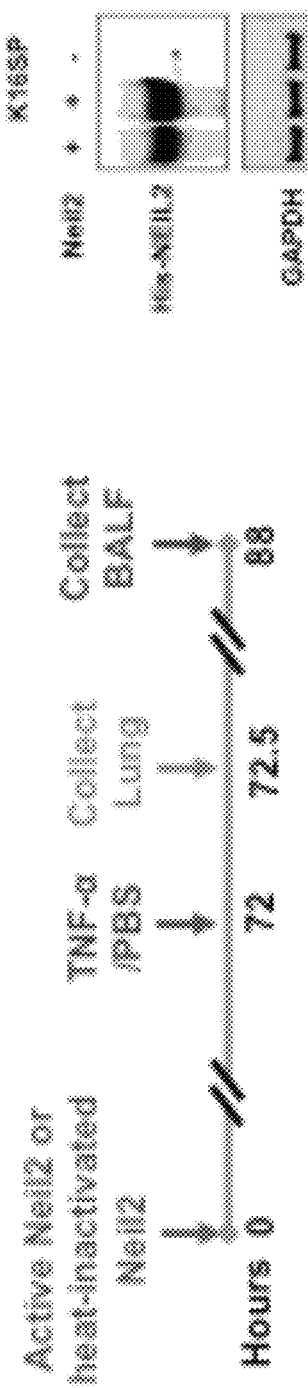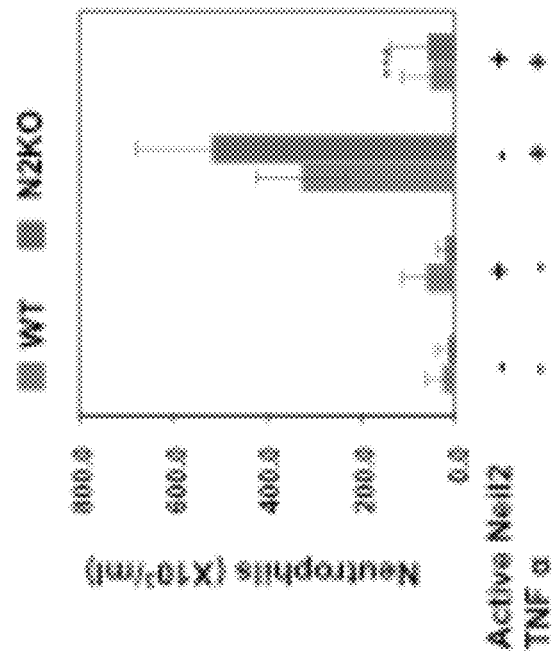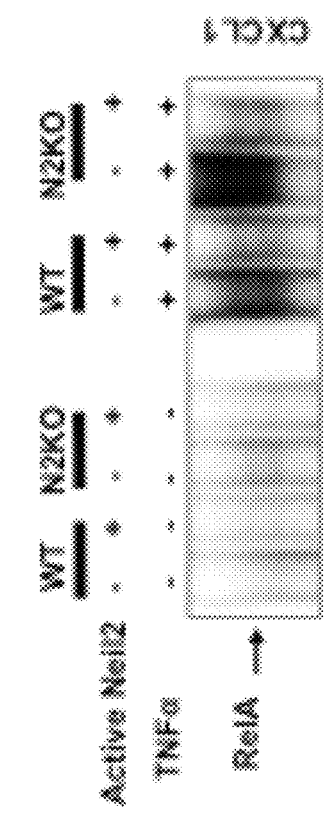
FIG. 8A
FIG. 8B
FIG. 8C
FIG. 8D

METHODS AND COMPOSITIONS RELATED TO RECOMBINANT NEIL2

CROSS REFERENCE TO RELATED APPLICATIONS

The present application is a divisional application of U.S. patent application Ser. No. 16/585,271 filed on Sep. 27, 2019 and claims priority to U.S. Provisional Application No. 62/738,605 filed Sep. 28, 2018, which is incorporated by reference herein in its entirety.

STATEMENT REGARDING FEDERALLY FUNDED RESEARCH

This invention was made with government support under NS073976 awarded by the National Institute of Neurological Disorders and Stroke (NINDS). The government has certain rights in the invention.

BACKGROUND OF THE INVENTION

I. Field of the Invention

The embodiments described herein generally concern the field of medicine and pathological inflammation. Particular embodiments are directed to compositions and methods for administering rNEIL2 to a subject in need.

II. Description of Related Art

Allergic asthma (AA) and allergic rhinitis (AR) are highly prevalent diseases of the airways, which are characterized by the presence of mucosal inflammation, reversible obstruction and airway hyperreactivity. These diseases have a significant impact on health, affecting 300 million (M) people worldwide and 22.2 M in the US, and the public health burden is increasing every year. Extensive research in the field has clearly indicated that airway epithelium-derived inflammation plays a sentinel role in asthma pathogenesis. Unlike other internal organs, the lungs are continuously exposed to environmental and occupational toxicants, the majority of which induce inflammation and generate reactive oxygen species (ROS). It is now widely accepted that inflammation underlies a wide variety of physiological and pathological processes including cancers. ROS generated due to normal cellular metabolism and/or dysregulated inflammatory response, are known to cause DNA base oxidation. Most of these DNA lesions are mutagenic and/or toxic and have been implicated in a wide variety of patho-physiological states, particularly cancer.

The rapid emergence of antibiotic resistant bacteria is occurring worldwide, and thus bacterial infections have become a real threat to our society. Many of these bacteria are already responsible for placing a substantial clinical and financial burden on the global as well U.S. health care system, patients, and their families. The crisis for developing bacterial resistance has been attributed to the overuse and misuse of various antibiotics, as well as a lack of development of new drug by the pharmaceutical industry due to a variety of reasons. Coordinated research efforts and new way of thinking are greatly needed to combat such untreatable organisms.

The World Health Organization (WHO) lists 12 bacteria that are in the priority pathogen list for R&D and new treatment modalities, other than antibiotics, are needed (available on the workd wide web at URL who.int/medicines/publications/WHO-PPL-Short_Summary_25Feb-ET_NM_WHO.pdf). *Klebsiella pneumoniae* (Kp) is on this priority list. It causes life-threatening infections, particularly in susceptible and immuno-compromised individuals. The general strategy used to fight high risk pathogens is use of antibiotics to which the bacteria is not resistant, reduce exposure, and is some situations, use vaccines or monoclonal antibodies.

There remains a need for additional methods of treating or ameliorating Allergic asthma (AA), allergic rhinitis (AR), and pathological inflammation of the lungs.

SUMMARY OF THE INVENTION

As described herein, evidence shows that delivering recombinant NEIL2 biologic into the lungs of the host as a paradigm-shifting strategy to reduce damage to the transcribed genome in the lungs; the lungs are able to accurately mount the innate immune response that is required to protect the host from fatality induced by lethal doses of a WHO priority pathogen. Certain embodiments of the current invention provide a solution to the problems associated with allergy and inflammation. In particular, pathological inflammation in the lungs.

As a proof-of principal, the inventors have developed Kp-infected animal model, and these animals die within 3-5 days of infection. Because of the emergence of multidrug resistance and tolerance, it is important to better understand the mechanisms and/or develop alternative strategy to combat such untreatable organisms. Severe bacterial infections induce DNA damage in the tissues, thus profoundly affecting the host's ability to mount an innate immune response required to destroy the pathogen. One way to fight the infection should be to correct the host's ability to repair its DNA accurately. The inventors investigate one such biologic, recombinant NEIL2 (rNEIL2), a DNA repair protein. It is shown that intracellular administration of rNEIL2 with a peptide carrier provided into the lung cells increased survival of animals to >60% against lethal *Klebsiella pneumoniae* infection 14 days after infection in mice.

Reactive oxygen species (ROS), generated endogenously under normal physiological conditions, and/or due to cellular responses to various xenobiotics, cytokines, and bacterial infection, target cellular macromolecules, including the genomic DNA. However, host cells are equipped with an arsenal of DNA repair proteins that continuously maintain genome's integrity for survival. ROS-induced oxidized DNA bases are primarily repaired via the base excision repair pathway, which is initiated with excision of the oxidized bases by a family of enzymes, called DNA glycosylases. The inventors cloned and were the first to report the role of NEIL2 in mammalian DNA-base excision repair, and demonstrated that NEIL2-null mice are much more responsive to inflammatory agents and also extremely susceptible to oxidative stress.

Bacterial infection induces severe inflammatory response which in turn can induce genome damage due to oxygen free radicals. The resultant accumulation of damage in the transcribed sequences can be lethal to host cells. It is contemplated that NEIL2 first repairs the oxidized DNA bases within the promoter regions and exons in the actively transcribing genes of innate immune response genes, and subsequently provides regulatory control of expression of those genes via interplay with NFκB. The inventors further contemplate that the coordinated action of these two NEIL2-dependent processes is responsible for maintaining the fidelity of a precise cassette of chemokines and will provide protective function against bacterial infection. This is a paradigm shift, and to our knowledge, the first example of maintaining genomic integrity of the host provides protection from an infection with a lethal pathogen.

Recombinant proteins are now widely used as therapeutic agents for ameliorating various diseases. The inventors, thus contemplate that delivering recombinant NEIL2 would be an effective therapeutic intervention in bacterial infection. Dr. Gobinda Sarkar's group (Mayo Clinic) has recently shown that synthetic peptide carriers can deliver small molecules and proteins to different tissues when administered intravenously without any toxic consequences. However, the inventors successfully delivered rNEIL2 to mouse lung with one peptide carrier (designated as K16SP). Most surprisingly, intracellular delivery of rNEIL2 into the lungs of mice provided strong protection against mortality in the *Klebsiella pneumoniae* (Kp) mediated pathogenic infection. Replicating bacteria trigger progressively increasing ROS-generation that can damage the genome of the host. Thus, a crucial component of the host immune response to robust bacterial infection must induce NEIL2-mediated TC-BER (transcription-coupled base excision repair) of the innate immune response genes. Given there is DNA damage accumulation in pathogenic infection, the investigators assessed the DNA damage accumulation in highly transcribing genes in the mouse lungs by LA-qPCR. Indeed, the investigators observed significant amount of oxidative genome damage after Kp infection, however, intranasal delivery of rNEIL2, prior to bacterial infection, efficiently repaired the transcribed genome. This led to the elevated CXCL1 mRNA levels that recruits neutrophils to clear the bacterial load leading to reduced mortality. Neutrophil recruitment is the hallmark of an innate immune response.

Using recombinant NEIL2 protein therapy against inflammatory diseases, bacterial infection, and asthma.

In certain aspects Nei-like protein 2 (NEIL2) or variant thereof has an amino acid sequence that is 90, 92, 94, 96, 98, 99, to 100% identical, including all values and ranges there between, over 50, 60, 70, 80, 90, 100, 110, 120, 130, 140, 150, or 155 contiguous amino acids, including all values and ranges there between to MPEGPLVRKFHHLVSPFVGQQVVKTGGSSKKLQPASLQSL WLQDTQVHGKKLFLRFDL DEEMGPPGSSPT-PEPPQKEVQKEGAADPKQVGEPSGQKTLDGSSR-SAELVPQGEDDSEY LERDAPAGDAGRWLRVSFGLFG SVWVNDFSRAKKANKRGDWRDPSPRLVLHFGGGGF LAFYNCQLSWSSSPVVTPTCDILSEKFHRGQALEAL-GQAQPVCYTLLDQRYFSGLGNIIK NEALYRAGIHP LSLGSVLSASRREVLVDHVVEFSTAWLQGKFQG RPQHTQVYQKEQCP AGHQVMKEAFGPEDG-LQRLTWWCPQCQPQLSEEPEQCQFS (Accession AAH13952.1 NEIL2 protein [*Homo sapiens*]) (SEQ ID NO:1). Other aspects are directed to an NEIL2 polypeptide, segment, or variant thereof having 10, 20, 30, 40, 50, 60, 70, 80, 90, 100, 110, 120, 130, 140, 150, or 155 contiguous amino acids (including all values and ranges there between) starting from or ending at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, or 332 of SEQ ID NO:1. The NEIL2 polypeptide, segment or variant at least, at most, or about 80, 85, 90, 92, 94, 69, 98, 99, to 100% identical to SEQ ID NO:1, including all values and ranges there between. Preferably, but not necessarily, the segment or variant is a functional segment or variant maintaining a DNA glycosylase activity. In still further aspects an NEIL2 polypeptide, segment or variant can be modified by chemical modification of amino acid side chains (e.g., crosslinking, glycosylation, etc.) or by including or coupling heterologous peptide sequences or targeting moieties at the amino or carboxy terminus of the peptide.

In certain embodiments a NEIL2 polypeptide, segment, or variant is coupled to a lung cell targeting moiety or a carrier peptide directly or indirectly. In some embodiments, the carrier peptide is selected from KKKKAAVALLPAVLLAL-LAPMSVLTPLLLRGLTGSARRLPVPRAKIHSL (SEQ ID NO:2); KKKKKKKKAAVALLPAVLLAL-LAPMSVLTPLLLRGLTGSARRLPVPRAKIHSL (SEQ ID NO:3); KKKKKKKKKKKKAAVALLPAVLLAL-LAPMSVLTPLLLRGLTGSARRLPVPRAKIHSL (SEQ ID NO: 4); KKKKKKKKKKKKKKKKAAVALLPAVLLAL-LAPMSVLTPLLLRGLTGSARRLPVPRAKIHSL (SEQ ID NO: 5); KKKKAAVALLPAVLLALLAP (SEQ ID NO: 6); KKKKKKKKAAVALLPAVLLALLAP (SEQ ID NO: 7); KKKKKKKKKKKKAAVALLPAVLLALLAP (SEQ ID NO: 8); KKKKKKKKKKKKKKKKAAVALLPAVLLAL-LAP (SEQ ID NO: 9); YKKKKKKKKKKKKKKK-KAAVALLPAVLLALLAP (SEQ ID NO: 10); KKKKKKKKKKKKKKKKAAVALLPAVLLALLAPA-AVALLPAVLLALLAP (SEQ ID NO: 11); AAVALLPAVL-LALLAPKKKKKKKKKKKKKAAVALLPAVLLALLAP (SEQ ID NO: 12); KKKKKKKKKKKKKKKKAAVWLL-WYVLLFLLYL (SEQ ID NO: 13); KKKKKKKKKKKKKKKKFWVWLLWYVLLFLLYL (SEQ ID NO:14). In a particular aspect the carrier peptide is SEQ ID NO:9 (K16SP peptide).

The invention relates to the use of recombinant NEIL2 (rNEIL2) to treat bacterial infections, inflammatory diseases, asthma, and allergen induced airway inflammation. NEIL2 was first shown by the inventors a DNA repair protein working through the Base Excision Repair pathway. There are two independent studies that are combined indications in one application.

In the first study, the inventors delivered rNEIL2 into the lungs of Kp infected mice, providing >60% survival to an otherwise lethal dose. It is hypothesized that rNEIL2 repairs the ROS-induced oxidized DNA bases in the promoter regions and exons of the actively transcribing genes of the innate immune response genes. The novelty of the invention is helping the host maintain genomic integrity by supplying increased rNEIL2. The invention is a method of treatment for bacterial infections and generation of rNEIL2.

In another study, the inventors showed NEIL2 plays a role in allergen induced airway inflammation. NEIL2 knockout mice were challenged with allergens after being administered rNEIL2. A significant decrease in eosinophil recruitment was seen in the rNEIL2 administered mice versus the NEIL2 knockout mice who did not receive rNEIL2 therapy.

Certain embodiments are directed to treatments for, but not limited to antibiotic resistant bacteria, Kp, allergen induced airway inflammation, allergic disorders (e.g., allergic rhinitis), asthma (e.g., allergic asthma).

Other embodiments of the invention are discussed throughout this application. Any embodiment discussed with respect to one aspect of the invention applies to other aspects of the invention as well and vice-a-versa. Each embodiment described herein is understood to be embodiments of the invention that are applicable to all aspects of the invention. It is contemplated that any embodiment discussed herein can be implemented with respect to any method or composition of the invention, and vice-a-versa.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "inhibiting" or "reducing" or "preventing" or any variation of these terms includes any measurable decrease or complete inhibition to achieve a desired result.

The term "effective," as that term is used in the specification and/or claims, means adequate to accomplish a desired, expected, or intended result.

The terms "wt. %," "vol. %," or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 1A) OFF and ON states of STAT6 and NFkB binding sites on the CCL 11 promoter. Chronic oxidative stress in sensitized mice and humans allows oxidatively damaged DNA base lesions (hexagon) to remain without repair in the CCL 11 promoter. NEIL2 stably docks on the lesion and prevents binding of NFkB and STAT6 (OFF STATE). Induction of intense oxidative stress by allergen challenge stimulates DNA-damage repair by a DG, generating strand breaks that release SSODDFs and NEIL2 (N2) from the promoter region. NEIL2-free promoter site now allows binding of STAT6 and NFkB (ON STATE), and allows transcription of CCL 11 and other STAT6- and NFkB-dependent genes. (FIG. 1B) Formation of a NEIL2-STING complex in the cytosol. RWPE/CDE challenge activates DGs that remove SSODDFs from the genome, that in turn stimulate formation of a NEIL2-SSODDF-STING complex in the cytosol on the SSODDF template. Complexing of NEIL2 with STING inhibits activation (phosphorylation) of NFkB and STAT6.

(FIGS. 2A-E) Effect of NEIL2 on CDE induced AIR in multiple challenge model. (FIG. 2A) Heat map of PCR array of lung mRNA of 84 allergy-associated genes. Three WT mice (labeled 1, 2, and 3) have a distinct pattern of gene expression from four Neil2 KO mice (labeled 5, 6, 7, and 8), seen in 4th panel from top (arrow) (FIG. 2B) qPCR analysis of lung CCL 11 mRNA expression. (FIG. 2C) BAL eosinophils numbers 72 hrs after the final COE challenge, n=5-6 per group (0). (FIG. 2D) Airway epithelium mucin score, wild type and Neil2 KO mice, n=5-6/group. (FIG. 2E) Lung histology, showing increased inflammation in Neil2 KO mice.

(FIG. 3A) CDE multiple challenge model, MCM. The mice were sensitized by 5 daily CDE challenges (100 μg), followed by a rest period of 7 days, 11 d, indicated as 11 d in FIGS. 3B, 3C, 4B, 4D, and 4E). All other time points start after a subsequent $6^{th}$ challenge, with groups sacrificed at 30 mins (+30 m), +1 h, +4 h and +72 h after the 6 h challenge. (FIG. 3B) NEIL2 (upper panel) and NFkB (lower panel) ChTP analysis of the CCL 11 promoter. (FIG. 3C) NEIL2 (upper panel) and NFkB (lower panel) ChTP analysis of the CXCL 1 promoter. (FIG. 3D) EMSA assay of CCL 11 probe with 11 d lung nuclear extract from WT and Neil2KO multiple challenge mice. (FIG. 3E) Inhibition of binding of NFkB in EMSA of Neil2KO extracts by different doses of rNEIL2. (FIGS. 3F, 3G, 3H) Effect of recombinant NEIL2 (rNEIL2) on allergic inflammation. C57BL/6J mice were sensitized to CDE with intraperitoneal CDE+alum×2, and given intranasal Chariot protein transfection reagent (CDE, n=4) or Chariot+rNeil2 (CDE+rNeil2, n=3) 1 h prior to the final challenge with intranasal CDE (F) 72 hrs later WB of lungs for HIS-tagged rNEIL2 confirms presence of rNEIL2 at 72 h in three mice that received Chariot+rNEIL2. WT; BAL total cells (FIG. 3G) and eosinophils (FIG. 3H).

FIGS. 4A-E. Role of NEIL2 in protein interactions and activation in COE SCM and MCM. (FIGS. 4A, 4B) Interaction of proteins in the lung cell cytosol. (FIG. 4A) Single challenge model. There is complete lack of protein-protein interaction between NEIL2 and other proteins in the cytosolic fraction of lung lysates at any time point after a single CDE challenge in WT mice. (FIG. 4B) MCM. There is strong protein-protein interaction of NEIL2 with STING and IRF3 at all time points in the cytosolic fraction of lung lysates after multiple CDE challenges in WT mice. DNAse treatment abolished the association of NEIL2 with STING at all time points in the STING input region. IgG control IPs did not show any bands (data not shown). (FIGS. 4C, 4D) NEIL2, NFkB, and STAT6 WBs of nuclear extracts of lungs after a single CDE challenge (FIG. 4C) or multiple CDE challenges. (FIG. 4D) After a single challenge, levels of these proteins do not change. By contrast, there was a striking change after multiple challenges. (FIG. 4E) pSTAT6 levels in lung nuclear extracts. pSTAT6 persisted in the nucleus for 4 h only in the Neil2KO multiple-challenge model.

(FIG. 5A) TNSS components (nasal itching, runny nose, sneezing, and nasal congestion; (FIG. 5B) Heat map of z score values of differentially expressed genes in RNAseq analysis of Rhino-probe samples from four NC subjects (N1-N4) and two AR subjects (A1, A2) at baseline and 3 hrs after RWP exposure. (FIG. 5C) Nasal curette samples from NC and AR subjects sampled when there was virtually no detectable atmospheric pollen count were subjected to NEIL2 IP and STING WB. Even though NC had slightly greater input STING, the amount of STING IP'd with NEIL2 was much greater in AR than NC. The levels of NEIL2 were identical.

(FIG. 7A) mRNA expression of CXCL1 in lung tissue after TNFα challenge of WT or Neil2KO mice. (FIG. 7B) WT and Neil2KO mice were challenged intranasally with mock- or TNFα, and ChIP was performed from lung extracts at 0, 15, 30, and 60 min using anti-RelA (NF-κB) antibody (Left panel), and anti-NEIL2 antibody (right panel).

FIG. 8A-D. (FIG. 8A) Experimental design for intranasal delivery of rNEIL2. (FIG. 8B) Western blot from mouse lungs to show K16SP-mediated delivery of rNEIL2 (72 h post-delivery). Mock represents only PBS treatment. (C) Gel shift assays with nuclear extract incubated with radiolabeled CXCL1 DNA probes. (D) Neutrophil count after rNEIL2 delivery.

(FIG. 9A) Kaplan Meier plot of Kp-induced fatality in mice. (FIG. 9B) Assessment of genomic integrity of the transcribed genome of POLB gene. (FIG. 9C) Effect of administering rNEIL2 on lung neutrophil counts in Kp infected mice (lower panel). Western blot showing the presence of rNEIL2 in mouse lungs (Upper panel). (FIG. 9D) Effect of administering rNEIL2 on CXCL1 expression levels in Kp infected mouse lungs.

DETAILED DESCRIPTION OF THE INVENTION

Figures 1A, 1B:
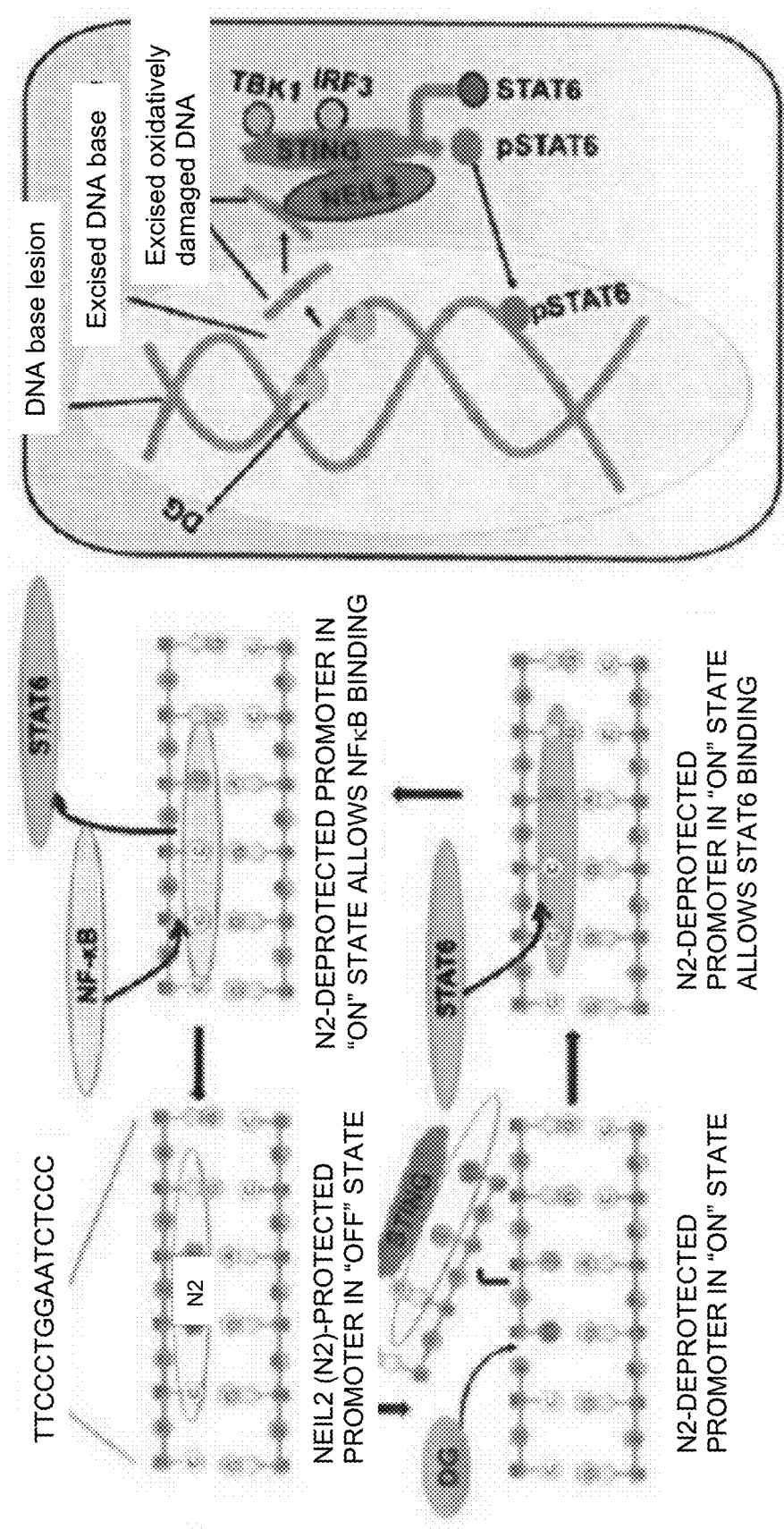
FIGS. 1A-B. Role of NEIL2 in allergen-induced IIR and AIR.

Ragweed pollen (RWP) and cat dander are major allergens associated with AA and AR. The innate pathways that provide protection against innate (IIR) and allergic (AIR) immune/inflammatory airway responses induced by these and other allergens are of great scientific interest. The inventors made a surprising observation that Nei-like 2 (NEIL2), which the inventors cloned and characterized, stably associates with the cytosolic DNA sensor Stimulator of Interferon Genes complex (STING) only in allergic mice and human subjects, and intrapulmonary administration of recombinant (r)NEIL2 markedly decreases cat dander extract (CDE)-induced AIR. The central hypothesis is that NEIL2 protects against allergen-induced gene transcription, IIR and AIR in sensitized mice and humans by: (i) binding to the promoter region of specific genes in the nucleus and (ii) complexing with STING in the cytosol. Binding of NEIL2, STAT6- and NFkB to the promoter regions of genes and the type of oxidatively damaged DNA base lesions in the genome can be assessed in nasal curette samples from allergic and healthy human subjects, and lung tissues from wild type (WT) and Neil2KO mice to detect NEIL2 binding to the promoter regions of STAT6- and NFkB-dependent genes, and protects against recruitment of these transcription factors (TFs) and inhibits allergen-induced gene expression and AIR. WT recombinant (r) NEIL2$^{WT}$ and active site mutant rNEIL2$^{ASM}$ can be administered into the lungs of sensitized Neil2KO mice, and their ability to bind to promoter sites and inhibit IIR and AIR elucidated. Nasal curette samples from healthy and allergic human subjects and lung tissues from non-sensitized and sensitized mice can be analyzed to determine the nucleotide sequence of cytosolic single-strand DNA fragments, and elucidate protein-protein interactions of NEIL2 with the STING complex, gene expression, IIR and AIR to confirm that NEIL2 associates with the STING complex in the cytosol of AECs and inhibits allergen-induced STING-activation and AIR. In Neil2KO mice, rNEIL2, rNEIL2$^{ASM}$. and in WT and Neil2KO mice specific DNA damage-containing engineered oligos can be administered with single/multiple CDE challenges, and the domains of rNEIL2 and DNA damage lesions required for NEIL2 to interact with STING and modulate genome-wide gene expression, IIR and AIR can be determined. Further studies can be performed to confirm that NEIL2 stably associates with STING in the nasal epithelial cells of subjects with allergic rhinitis and non-allergic rhinitis with eosinophilia syndrome, NARES, but not normal control (NC) subjects, and exposure of AR but not NC subjects to RWP in a pollen exposure chamber (PEC) displaces NEIL2 from the promoter regions of NFkB- and STAT6-dependent genes in nasal epithelial cells. Thus, recombinant NEIL2 can be developed as a therapeutic agent to prevent AIR in atopic subjects.

I. Recombinant NEIL2 Polypeptides

Recombinant proteins are now widely used as therapeutic agents for ameliorating various diseases. The Inventors have studied recombinant NEIL2 (SEQ ID NO:1) as a therapeutic intervention in bacterial infection. Synthetic peptide carriers can deliver small molecules and proteins to different tissues when administered intravenously without any toxic consequences. However, the inventors successfully delivered rNEIL2 to mouse lung a K16SP peptide carrier (a gift from Dr. Sarkar). Most surprisingly, intracellular delivery of rNEIL2 into the lungs of mice provided strong protection against mortality in the *Klebsiella pneumoniae* (Kp) mediated pathogenic infection. Replicating bacteria trigger progressively increasing ROS-generation that can damage the genome of the host. Thus, a crucial component of the host immune response to robust bacterial infection must induce NEIL2-mediated TC-BER (transcription-coupled base excision repair) of the innate immune response genes. Given there is DNA damage accumulation in pathogenic infection, the Inventors assessed the DNA damage accumulation in highly transcribing genes in the mouse lungs by LA-qPCR. Indeed, a significant amount of oxidative genome damage was observed after Kp infection; however, intranasal delivery of rNEIL2, prior to bacterial infection, efficiently repaired the transcribed genome. This led to the elevated CXCL1 mRNA levels that recruits neutrophils to clear the bacterial load leading to reduced mortality. Neutrophil recruitment is the hallmark of an innate immune response.

Amino acid sequence variants or derivatives of the proteins, polypeptides and peptides of the present invention can be substitutional, insertional or deletion variants, as well as inclusion of amino acid analogs or derivatives. Deletion variants lack one or more residues of the native protein that are not essential for function or immunogenic activity. Another common type of deletion variant is one lacking secretory signal sequences or signal sequences directing a protein to bind to a particular part of a cell or membrane spanning regions or other functional sequences not needed for the in vivo activity sought. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within a polypeptide or peptide, and may be designed to modulate one or more properties, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, a biologically functional equivalent will have a sequence of about 70, 75, 80, 85, 90, 95, 96, 97, 98, 99% of amino acids that are identical or functionally equivalent to the amino acids of a polypeptide or peptide or variant or analog or derivative thereof and provide a similar biological activity/response to flagellin or other toll-like receptor (TLR) agonist.

In certain embodiments a rNEIL2 polypeptide, segment or variant is coupled, covalently or non-covalently with a carrier peptide. A carrier peptide can include, but is not limited to a peptide comprising one or more of a transport peptide; a peptide cleavage sequence; a nuclear localization sequence; and SP is a signal peptide.

A transport protein can be lysine or a non-natural lysine derivative, arginine or a non-natural arginine derivative, and combinations thereof. In some embodiments, the transport protein can be a sequence of four or more lysine residues or a sequence of 4 or more arginine residues. Non-limiting examples of transport proteins can include KKKK (SEQ ID NO: 15); KKKKKKKK (SEQ ID NO:16); KKKKKKKKKKKK (SEQ ID NO:17); KKKKKKKKKKKKKKKK (SEQ ID NO:18); RRRR (SEQ ID NO: 19); RRRRRRRR (SEQ ID NO: 20); RRRRRRRRRRRR (SEQ ID NO: 21); RRRRRRRRRRRRRRRR (SEQ ID NO: 22); KRKR (SEQ ID NO: 23); KKKR (SEQ ID NO: 24); KKKRRRKKKRRR (SEQ ID NO: 25); and KKKKRRRRKKKKRRRR (SEQ ID NO: 26).

A peptide cleavage sequence (PCS) can be any suitable sequence that once in the cell can be enzymatically cleaved from the remaining sequence. In some embodiments, the PCS can include a furin protease cleavage recognition sequence. In other embodiments, the PCS is XRXLRRX (SEQ ID NO: 27), wherein X is a hydrophobic amino acid (e.g., V, I, L, M, F, W, C, A, Y, H, T, S, P, or G).

A nuclear localization sequence (NLS) can be any sequence suitable for targeting the carrier peptide from the cytoplasm into the nucleus of the cell across the nuclear membrane. Any peptide, derivative thereof, or peptide analogue that functions to transport an associated molecule through a nuclear membrane can be used. Certain preferred specific NLSs include PKKKRKV (SEQ ID NO: 28) which is a monopartite NLS from SV40 large T antigen, LVRKKRKTEEESPLKDKDAKKSKQE (SEQ ID NO:29) which is a bipartite NLS from SV40 N1 protein, and PEVKKKRKPEYP (SEQ ID NO: 30).

A signal peptide (SP) can be any sequence capable of translocating across the cell membrane into the interior of the selected target cell. In some cases, a SP is capable of translocating into the interior of an organelle (e.g., mitochondrion or nucleus). For example, a SP can comprise the sequence: $X_1X_2VX_3LLX_4X_5VLLX_6LLX_7X_8$ (SEQ ID NO: 31) wherein $X_1$-$X_8$ are independently L, A, W, F, Y, or V. In some embodiments, $X_1$ is A or F; $X_2$ is A or W; $X_3$ is A or W; $X_4$ is P or W; $X_5$ is A or Y; $X_6$ is A or F; $X_7$ is A or Y; $X_8$ is P or L. In some cases, the SP is AAVALLPAVLLAL-LAP (SEQ ID NO:32). In another embodiment, the SP is AAVALLPAVLLALLAPMSVLTPLLLR-GLTGSARRLPVPRAKIHSL (SEQ ID NO: 33).

The peptides disclosed herein are described using the standard one letter amino acid abbreviations. The amino acids can be in their D or L form. All peptides can be prepared using methods known to those having ordinary skill in the art, including solid phase methods.

Further provided herein are complexes comprising a biologically active molecule associated with a carrier peptide. In some embodiments, the biologically active molecule is non-covalently bound to the carrier peptide. A carrier peptide can comprise any sequence as described previously.

"Associated with" or "coupled to" as used herein is meant that the biologically active molecule is conjugated to the carrier peptide in such a manner that when the carrier peptide crosses the cell membrane, the molecule is also imported across the cell membrane. In certain embodiments, the biologically active molecule is non-covalently bound to the carrier peptide. In other embodiments, the carrier peptide may be covalently bound, either directly or indirectly (e.g., through a linker), to the biologically active molecule.

A linker can be any moiety suitable for linking a carrier peptide to a biologically active molecule. A linker can be bound at the C-terminus, the N-terminus, or both, of a carrier peptide. Additionally, a linker can be bound to the side chain of a carrier peptide. If a carrier peptide is bound to multiple linkers, each linker can be different. A linker can be covalently linked to a side chain of an amino acid, e.g., lysine, glutamine, cysteine, methionine, glutamate, aspartate, asparagine.

In some embodiments an amino acid side chain can serve as the linker. For example the epsilon amino group ($\epsilon$-$NH_2$) can be used to conjugate to a carrier for instance through an amide or thiourea linkage. Similarly the delta amino group of ornithine (orn), the gamma amino group of diaminobutyric acid (dab), or the beta amino group of diamino proprionic acid (dpr) can also act as linkers. These amino acids may be at the C- or N-terminus of the carrier peptide or they may be positioned within the carrier peptide sequence.

A. Polypeptide Composition and Formulations

"Polypeptide" refers to any peptide or protein comprising amino acids joined by peptide bonds or modified peptide bonds. "Polypeptide" refers to short chains, including peptides, oligopeptides or oligomers, and to longer chains, including proteins. Polypeptides may contain amino acids other than the 20 gene-encoded amino acids. "Polypeptides" include amino acid sequences modified either by natural processes, such as post-translational processing, or by chemical modification or other synthetic techniques well known in the art. Modifications can occur anywhere in a polypeptide, including the peptide backbone, the amino acid side-chains, and the amino terminus or the carboxy terminus. It will be appreciated that the same type of modification may be present in the same or varying degrees at several sites in a given polypeptide. Also, a given polypeptide may contain many types of modifications. Modifications include terminal fusion (N- and/or C-terminal), acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a subject as an isolated polypeptide; in other words, the polypeptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

The term "amino acid" or "residue" should be understood to mean a compound containing an amino group ($NH_2$), a carboxylic acid group (COOH), and any of various side groups, that have the basic formula $NH_2CHRCOOH$, and that link together by peptide bonds to form proteins. Amino acids may, for example, be acidic, basic, aromatic, polar or derivatized. Non-standard amino acids may be referred to as "non-canonical" amino acids. Amino acids are naturally found in the $\alpha$- and L-form, however, $\beta$- and D-form amino acids can also be prepared.

A one-letter abbreviation system is frequently applied to designate the identities of the twenty "canonical" amino acid residues generally incorporated into naturally occurring peptides and proteins, these designation are well known in the art. Such one-letter abbreviations are entirely interchangeable in meaning with three-letter abbreviations, or non-abbreviated amino acid names. The canonical amino acids and their three letter and one letter codes include Alanine (Ala) A, Glutamine (Gln) Q, Leucine (Leu) L, Serine (Ser) S, Arginine (Arg)R, Glutamic Acid (Glu) E, Lysine (Lys) K, Threonine (Thr) T, Asparagine (Asn) N, Glycine (Gly) G, Methionine (Met) M, Tryptophan (Trp) W, Aspartic Acid (Asp) D, Histidine (His) H, Phenylalanine (Phe) F, Tyrosine (Tyr) Y, Cysteine (Cys) C, Isoleucine (Ile) I, Proline (Pro) P, and Valine (Val) V.

Certain embodiments also include variants of the polypeptides described herein. Variants of the disclosed polypeptides may be generated by making amino acid additions or insertions, amino acid deletions, amino acid substitutions, and/or chemical derivatives of amino acid residues within the polypeptide sequence. Desired amino acid substitutions (whether conservative or non-conservative) can be determined by those skilled in the art in accordance with guidance provided herein for increasing stability, while maintaining or enhancing potency of the polypeptides. In certain embodiments, conservative amino acid substitutions can encompass non-naturally occurring amino acid residues which are typically incorporated by chemical peptide synthesis rather than by synthesis in biological systems.

Conservative modifications can produce peptides having functional, physical, and chemical characteristics similar to those of the peptide from which such modifications are made. In contrast, substantial modifications in the functional and/or chemical characteristics of peptides may be accomplished by selecting substitutions in the amino acid sequence that differ significantly in their effect on maintaining (a) the structure of the molecular backbone in the region of the substitution, for example, as an $\alpha$-helical conformation, (b) the charge or hydrophobicity of the molecule at the target site, or (c) the size of the molecule. For example, a "conservative amino acid substitution" may involve a substitution of a native amino acid residue with a non-native residue such that there is little or no effect on the polarity or charge of the amino acid residue at that position.

Recombinant DNA- and/or RNA-mediated protein expression and protein engineering techniques, or any other methods of preparing peptides, are applicable to the making of the polypeptides disclosed herein or expressing the polypeptides disclosed herein in a target cell or tissue. The term "recombinant" should be understood to mean that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well-known molecular biological procedures. Examples of such molecular biological procedures are found in Maniatis et al., *Molecular Cloning. A Laboratory Manual*, Cold Spring Harbor Laboratory, Cold Spring Harbor, N.Y., 1982. A "recombinant DNA molecule," is comprised of segments of DNA joined together by means of such molecular biological techniques. The term "recombinant protein" or "recombinant polypeptide" as used herein refers to a protein molecule that is expressed using a recombinant DNA molecule. A "recombinant host cell" is a cell that contains and/or expresses a recombinant nucleic acid.

The polypeptides can be made in transformed host cells according to methods known to those of skill in the art. Briefly, a recombinant DNA molecule, or construct, coding for the peptide is prepared. Methods of preparing such DNA molecules are well known in the art. For instance, sequences encoding the peptides can be excised from DNA using suitable restriction enzymes. Any of a large number of available and well-known host cells may be used in the practice of various embodiments. The selection of a particular host is dependent upon a number of factors, which include, for example, compatibility with the chosen expression vector, toxicity of the polypeptides encoded by the DNA molecule, rate of transformation, ease of recovery of the polypeptides, expression characteristics, bio-safety, and costs. A balance of these factors should be struck with the understanding that not all hosts may be equally effective for the expression of a particular DNA sequence. Within these general guidelines, useful microbial host cells in culture include bacteria (such as *Escherichia coli*), yeast (such as *Saccharomyces* sp.) and other fungal cells, insect cells, plant cells, mammalian (including human) cells, e.g., CHO cells and HEK293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired polypeptides are expressed. In addition, the DNA optionally further encode, 5' to the coding region of a fusion protein, a signal peptide sequence (e.g., a secretory signal peptide) operably linked to the expressed polypeptide.

The polypeptides can also be made by synthetic methods. Solid phase synthesis can be used as a technique of making individual polypeptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Suitable techniques are well known in the art. See, e.g., Merrifield, *Chem. Polypeptides*, Katsoyannis and Panayotis eds., pp. 335-361, 1973; Merrifield, *J. Am. Chem. Soc.* 85: 2149, 1963; Davis et al., *Biochem. Intl.* 10:394-414, 1985; Stewart and Young, *Solid Phase Peptide Synthesis*, 1969; U.S. Pat. No. 3,941,763; Finn et al., *The Proteins*, 3rd ed., 2:105-253, 1976; and Erickson et al., *The Proteins*, 3rd ed., 2: 257-527, 1976; "Protecting Groups in Organic Synthesis," 3rd ed., T. W. Greene and P. G. M. Wuts, Eds., John Wiley & Sons, Inc., 1999; NovaBiochem Catalog, 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Protecting Groups," P. J. Kocienski, Ed., Georg Thieme Verlag, Stuttgart, Germany, 1994; "Fmoc Solid Phase Peptide Synthesis, A Practical Approach," W. C. Chan and P. D. White, Eds., Oxford Press, 2000; G. B. Fields et al., Synthetic Peptides: A User's Guide, 77-183, 1990.

There are a wide variety of detectable labels that can be attached to polypeptides and variants thereof. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCPCy5.5, PE-Cy5, PE-Cy5.5, PE-Cy7, PE-Texas Red, and APC-Cy7. Other fluorophores include, inter alia, Alexa Fluor® 350, Alexa Fluor® 488, Alexa 25 Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7. For secondary detection using labeled avidin, streptavidin, captavidin or neutravidin, the polypeptides can usefully be labeled with biotin. Polypeptides can be labeled with radioisotopes, such as $^{33}$P, $^{32}$P, $^{35}$S, $^{3}$H, and $^{125}$I. As another example, when the polypeptide may be used for targeted radiotherapy, the label can be $^{3}$H, $^{228}$Th, $^{227}$Ac, $^{225}$Ac, $^{223}$Ra, $^{213}$Bi, $^{212}$Pb, $^{212}$Bi, $^{211}$At, $^{203}$Pb, $^{194}$Os, $^{188}$Re, $^{186}$Re, $^{153}$Sm, $^{149}$Tb, $^{131}$I, $^{125}$I, $^{111}$In, $^{105}$Rh, $^{99m}$Tc, $^{97}$Ru, $^{90}$Y, $^{90}$Sr, $^{88}$Y, $^{72}$Se, $^{67}$Cu, or $^{47}$Sc.

A composition that includes a polypeptide covalently linked, attached, or bound, either directly or indirectly through a linker moiety, to another peptide, vehicle (e.g., carrier), or a half-life extending moiety is a "conjugate" or "conjugated" molecule, whether conjugated by chemical means (e.g., post-translationally or post-synthetically) or by recombinant fusion. Conjugation of the polypeptides can be via the N-terminus and/or C-terminus of the polypeptide, or can be intercalary as to the peptide's primary amino acid sequence. A linker can be used to create fusion protein(s) that allow introduction of additional moieties to enhance uptake or localization of a polypeptide.

In some embodiments, a polypeptide is coupled to or encapsulated in a delivery vehicle, such as a carrier (e.g., a particle), or a liposome. In some embodiments, coupling of the polypeptide to the carrier includes one or more covalent and/or non-covalent interactions. In one embodiment the carrier is a metallic or polymeric particle. In one embodiment, the carrier is a liposome. The particles can be microscopic or nanoscopic in size. In certain aspects a particle has a diameter of from at least, at most, or about 0.1 µm to at least, at most, or about 10 µm. In another aspect, the particle has an average diameter of at least, at most, or about 0.3 μm to at least, at most, or about 5 μm, 0.5 μm to at least, at most, or about 3 μm, or 0.2 μm to at least, at most, or about 2 μm. In certain aspects the particle can have an average diameter of at least, at most, or about 0.1 μm, or at least, at most, or about 0.2 μm or at least, at most, or about 0.3 μm or at least, at most, or about 0.4 μm or at least, at most, or about 0.5 μm or at least, at most, or about 1.0 μm or at least, at most, or about 1.5 μm or at least, at most, or about 2.0 μm or at least, at most, or about 2.5 μm or at least, at most, or about 3.0 μm or at least, at most, or about 3.5 μm or at least, at most, or about 4.0 μm or at least, at most, or about 4.5 μm or at least, at most, or about 5.0 μm, including all values and ranges there between.

In some embodiments, the charge of a carrier (e.g., positive, negative, neutral) is selected to impart application-specific benefits (e.g., physiological compatibility, beneficial surface-peptide interactions, etc.). In some embodiments, a carrier has a net neutral or negative charge (e.g., to reduce non-specific binding to cell surfaces which, in general, bear a net negative charge). In some instances, a carrier is coupled to multiple polypeptides and can have 2, 3, 4, 5, 6, 7, 8, 9, 10 . . . 20 . . . 50 . . . 100, or more copies of a certain polypeptide or combinations of polypeptides exposed on the surface. In some embodiments, a carrier displays a single type of polypeptide.

The terms "packaged", "encapsulation" and "entrapped," as used herein, refer to the incorporation or association of a polypeptide in or with a liposome or similar vehicle. The polypeptide may be associated with the lipid bilayer or present in the aqueous interior of the liposome, or both.

The liposomes can be formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream. Various types of lipids are used to produce liposomes. For example, amphipathic lipids that find use are zwitterionic, acidic, or cationic lipids. Examples of zwitterionic amphipathic lipids are phosphatidylcholines, phosphatidylethanolamines, sphingomyelins, etc. Examples of acidic amphipathic lipids are phosphatidylglycerols, phosphatidylserines, phosphatidylinositols, phosphatidic acids, etc. Examples of cationic amphipathic lipids are diacyl trimethylammonium propanes, diacyl dimethylammonium propanes, stearylamine, etc. Examples of neutral lipids include diglycerides, such as diolein, dipalmitolein, and mixed caprylin-caprin; triglycerides, such as triolein, tripalmitolein, trilinolein, tricaprylin, and trilaurin; and combinations thereof. Additionally, cholesterol or plant sterols are used in some embodiments, e.g., to make multivesicular liposomes. A variety of methods are available for preparing liposomes as described in, e.g., Szoka et al., *Ann. Rev. Biophys. Bioeng.* 9:467 (1980), U.S. Pat. Nos. 4,235,871; 4,501,728; and 4,837,028, all of which are incorporated herein by reference.

"Unilamellar liposomes," also referred to as "single lamellar vesicles," are spherical vesicles that include one lipid bilayer membrane that defines a single closed aqueous compartment. The bilayer membrane includes two layers (or "leaflets") of lipids; an inner layer and an outer layer. The outer layer of the lipid molecules is oriented with the hydrophilic head portions toward the external aqueous environment and the hydrophobic tails pointed downward toward the interior of the liposome. The inner layer of the lipid lay directly beneath the outer layer with the lipids oriented with the heads facing the aqueous interior of the liposome and the tails oriented toward the tails of the outer layer of lipid.

"Multilamellar liposomes" also referred to as "multilamellar vesicles" or "multiple lamellar vesicles," include more than one lipid bilayer membrane, which membranes define more than one closed aqueous compartment. The membranes are concentrically arranged so that the different membranes are separated by aqueous compartments, much like an onion.

B. Expression and Expression Vectors

Polypeptide(s) described herein can be encoded by a nucleic acid that can in turn be inserted into or employed with a suitable expression vector or system. Recombinant expression can be accomplished using a vector, such as a plasmid, virus, etc. The vector can include a promoter operably linked to nucleic acid encoding one or more polypeptides. The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying, encoding and/or expressing nucleic acids encoding proteases can be produced. Such expression vectors include, for example, pET, pET3d, pCR2.1, pBAD, pUC, and yeast vectors. The vectors can be used, for example, in a variety of in vivo and in vitro situations. The vector may be a gene therapy vector, for example an adenovirus vector, a lentivirus vector or a CRISP-R vector.

The expression cassette, expression vector, and sequences in the cassette or vector can be heterologous to a particular nucleic acid or cell. As used herein, The term "heterologous" when used with respect to a nucleic acid (DNA or RNA) or protein refers to a nucleic acid or protein (also named polypeptide or enzyme) that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are typically not endogenous to the cell into which it is introduced, but has been obtained from another cell or synthetically or recombinantly produced. An expression cassette, expression vector, regulatory sequence, promoter, or nucleic acid can refer to an expression cassette, expression vector, regulatory sequence, or nucleic acid that has been manipulated in some way. For example, a heterologous promoter can be a promoter that is not naturally linked to a nucleic acid to be expressed, or that has been introduced into cells by cell transformation procedures. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous nucleic acids may comprise sequences that comprise cDNA. Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that are linked to a coding region to which they are not linked in nature.

Viral vectors that can be employed include those relating to lentivirus, adenovirus, adeno-associated virus, herpes virus, vaccinia virus, polio virus, human immunodeficiency virus, neuronal trophic virus, Sindbis and other viruses. Also useful are any viral families which share the properties of these viruses which make them suitable for use as vectors. Retroviral vectors that can be employed include those described in by Verma, I. M., Retroviral vectors for gene transfer. In Microbiology-1985, American Society for Microbiology, pp. 229-232, Washington, (1985).

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleic acid segment encoding a rNEIL2 or variant thereof. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3' to the transcription unit. They are usually between 10 and 300 nucleotides in length, and they function in cis. Enhancers function to increase transcription from nearby promoters.

Expression vectors used in eukaryotic host cells (yeast, fungi, insect, plant, animal, human or nucleated cells) can also contain sequences necessary for the termination of transcription which can affect mRNA expression. The 3' untranslated regions can also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the expression constructs.

The expression of rNEIL2 or variant thereof from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV.

The expression cassette or vector can include nucleic acid sequence encoding a marker product. This marker product is used to determine if the gene has been delivered to the cell and once delivered is being expressed. Preferred marker genes are the *E. coli* lacZ gene, which encodes β-galactosidase, and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells that have a novel gene would express a protein conveying drug resistance and would survive the selection. Examples of such dominant selection use the drugs neomycin (Southern and Berg, *J. Molec. Appl. Genet.* 1:327 (1982)), mycophenolic acid, (Mulligan and Berg, *Science* 209:1422 (1980)) or hygromycin, (Sugden, et al., *Mol. Cell. Biol.* 5: 410-13 (1985)).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes or viruses. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, (1993)). Appropriate means for transfection, including viral vectors, chemical transfectants, or physico-mechanical methods such as electroporation and direct diffusion of DNA, are described by, for example, Wolff et al., *Science,* 247, 1465-1468, (1990); and Wolff, *Nature,* 352, 815-818, (1991).

For example, the nucleic acid molecule, expression cassette and/or vector encoding a rNEIL2 or variant thereof can be introduced to a cell by any method including, but not limited to, calcium-mediated transformation, electroporation, microinjection, lipofection, particle bombardment and the like. The cells can be expanded in culture and then administered to a subject, e.g., a mammal such as a human. The amount or number of cells administered can vary but amounts in the range of about $10^6$ to about $10^9$ cells can be used. The cells are generally delivered in a physiological solution such as saline or buffered saline. The cells can also be delivered in a vehicle such as a population of liposomes, exosomes or microvesicles.

The rNEIL2 or variant thereof can be produced by a transgenic cell that produces exosomes or microvesicles that contain the polypeptide. Exosomes and microvesicles mediate the secretion of a wide variety of proteins, lipids, mRNAs, and micro RNAs, interact with neighboring cells, and can thereby transmit signals, proteins, lipids, and nucleic acids from cell to cell (see, e.g., Shen et al., *J Biol Chem.* 286(16): 14383-395 (2011); Hu et al., *Frontiers in Genetics* 3 (2012); Pegtel et al., *Proc. Nat'l Acad Sci* 107(14): 6328-33 (2010); WO/2013/084000; each of which is incorporated herein by reference in its entirety.

Thus transgenic cells with a heterologous expression cassette or expression vector that expresses one or more protease can be administered to a subject and the exosomes produced by the transgenic cells deliver the rNEIL2 to an appropriate tissue (e.g., lung) or cell in a subject.

In accordance with the above, the present disclosure relates to methods to derive vectors, particularly plasmids, cosmids, viruses and bacteriophages used conventionally in genetic engineering and in gene therapy that comprise a nucleic acid molecule encoding the polypeptide sequence of a rNEIL2 defined herein. In certain cases, the vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods that are well known to those skilled in the art can be used to construct recombinant vectors. Alternatively, the recited nucleic acid molecules and vectors can be reconstituted into liposomes for delivery to target cells. The vectors containing the nucleic acid molecules of the disclosure can be transferred into the host cell by well-known methods, which vary depending on the type of cellular host.

Another aspect of the invention is directed to a gene therapy vector comprising a rNEIL2 gene construct. Gene therapy vectors are known in the art and include, but are not limited to, lentiviral vectors, adenoviral vectors, adeno-associated viral vectors, plasmids and the like. Construction of a gene therapy vector of the invention can be done by methods known in the art. In certain aspects a gene therapy vector can be administered in an amount of about, at most, or at least 10, 100, 1000, $1\times10^4$, $1\times10^5$, $1\times10^6$, $1\times10^7$, $1\times10^8$, $1\times10^9$, $1\times10^{10}$, $1\times10^{11}$, $1\times10^{12}$ viral particles (VP) or colony forming units (CFU), including all values and ranges there between.

As an example of a gene therapy vector a rNEIL expression cassette can be included in a lentiviral vector. The therapeutic vector can be transduced into cells ex vivo and the cells delivered to the patient or subject. Likewise, a therapeutic vector of the invention can be delivered directly to the patient.

II. Treatment of Inflammation (Allergic Asthma (AA) and/or Allergic Rhinitis (AR))

Allergic asthma (AA) and allergic rhinitis (AR) are highly prevalent diseases of the airways, which are characterized by the presence of mucosal inflammation, reversible obstruction and airway hyperreactivity. These diseases have a significant impact on health, affecting 300 million (M) people worldwide and 22.2 M in the US, and the public health burden is increasing every year. Extensive research in the field has clearly indicated that airway epithelium-derived inflammation plays a sentinel role in asthma pathogenesis. Unlike other internal organs, the lungs are continuously exposed to environmental and occupational toxicants, the majority of which induce inflammation and generate reactive oxygen species (ROS). It is now widely accepted that inflammation underlies a wide variety of physiological and pathological processes including cancers. ROS generated due to normal cellular metabolism and/or dysregulated inflammatory response, are known to cause DNA base oxidation. Most of these DNA lesions are mutagenic and/or toxic and have been implicated in a wide variety of pathophysiological states, particularly cancer.

These oxidized bases are repaired primarily via the DNA base excision repair (BER) pathway, which is initiated with the excision of the lesion by DNA glycosylases. The inventors were the first to identify and characterize a new family of DNA glycosylases (NEILs 1-3). The inventors have then shown that NEIL2 initiates transcription-coupled-BER for preferential repair of oxidized bases from the transcribed genes. Furthermore, the inventors recently generated Neil2-null mice and reported that they accumulate oxidized bases mostly in the transcribed genome, thus providing the first in vivo evidence for genomic region-specific repair of oxidized bases. Notably, these mice are highly responsive to various inflammatory agents. However, NEIL2's role in allergen-induced airway inflammation is unknown.

The inventors' preliminary studies have shown that when sensitized Neil2 KO mice are challenged with allergens, these agents stimulated greater allergic inflammation and CCL11 (eotaxin) mRNA expression in the lungs than in wild-type (WT) mice. Most surprisingly, intrapulmonary administration of recombinant NEIL2 into sensitized mice markedly reduced allergen-induced eosinophil recruitment, suggesting its therapeutic potential in AIR and asthma. We will further assess whether local administration of recombinant NEIL2, or a smaller biologically active peptide sequence of NEIL2, can significantly reverse allergen-induced airway inflammation and be used as therapeutic agents to prevent inflammation in these and other allergic disorders and asthma in humans.

Figure 2A:
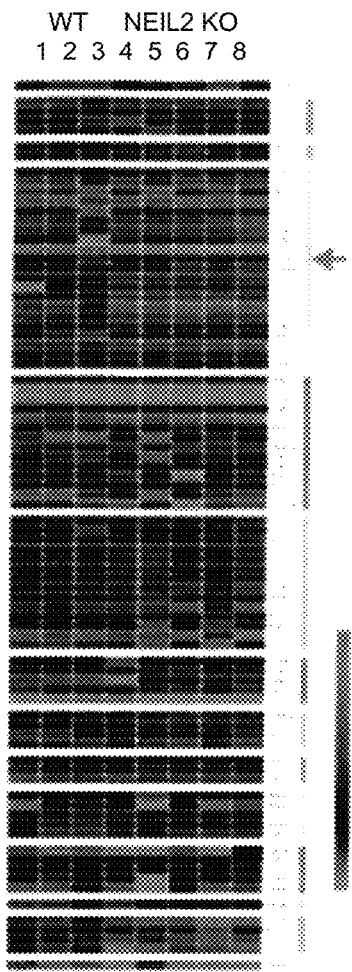
FIGS. 2A-E. Role of NEIL2 in CDE-AIR in mice.

NEIL2 binds to the promoter regions of STAT6- and NFkB-dependent genes and protects these regions from recruitment of these transcription factors (TFs) and inhibits allergen-induced immune response (AIR). NEIL2 modulates the binding of NFkB and STAT6 to their cognate sequence motifs. DNA damage is an ongoing normal and physiological cellular process for all aerobic organisms. Several reports have indicated that selective oxidation in the DNA sequence of a promoter element may be a mechanism for modulating gene expression by altering transcription factor binding (Ba et al. *J Immunol.* 2014,192(5):2384-94; Fleming et al. *PNAS* 2017,114(10):2604-9). Hence exploration of the role of base-excision repair (BER) enzymes, particularly the DNA glycosylases that initiate the repair process. A recent report has demonstrated that Neil2-null mice are susceptible to various inflammatory agents, such as TNFα and LPS (Chakraborty et al. *The Journal of biological chemistry.* 2015, 290(41):24636-48). Moreover, the inventors have found that these mice are also sensitive to RWPE and CDE, the two major allergens associated with asthma and allergic rhinitis. To examine the effect of NEIL2 in vivo on AIR, the inventors determined that multiple CDE challenges to Neil2KO mice elicited a distinct pattern of modulation of genes, shown in 4th panel (arrow) from the top in the PCR array (FIG. 2A), 5-fold greater CCL 11 expression (FIG. 2B), and greater eosinophil recruitment (FIG. 2C), airway mucin (FIG. 2D) and lung inflammation (FIG. 2E) compared to WT mice. These data indicate that NEIL2 potently inhibits AIR.

Figure 2B:
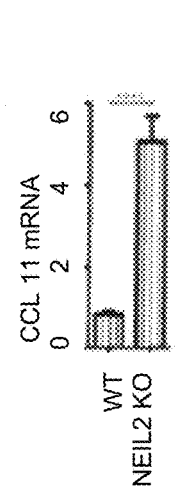
Figure 2C:
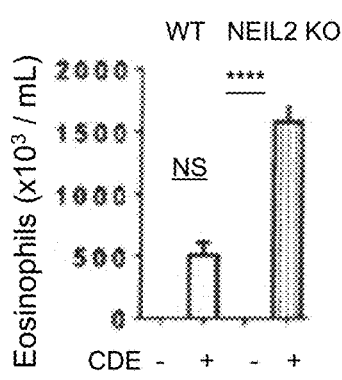
Figure 2D:
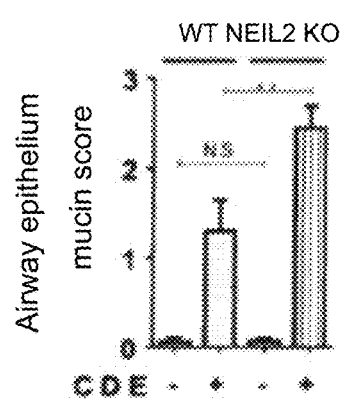
Figure 2E:
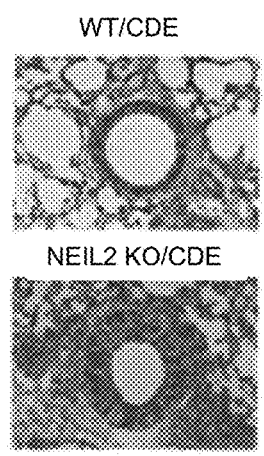
Figure 3A:
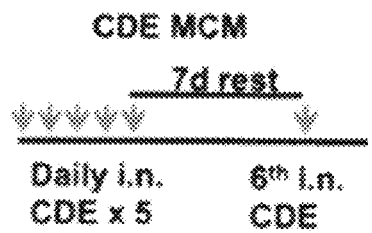
FIGS. 3A-H. ChIP and EMSA analysis of CDE multiple-challenge rNEIL2 F coE model in lungs.
Figure 3B:
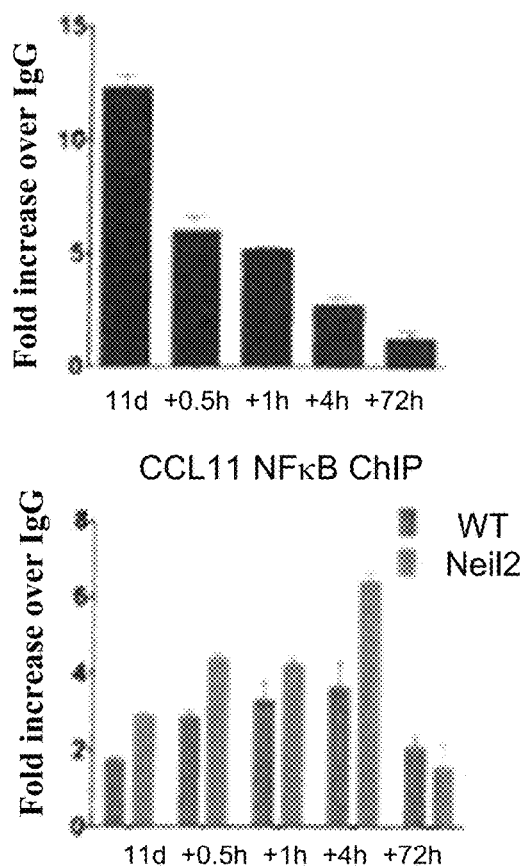
Figure 3C:
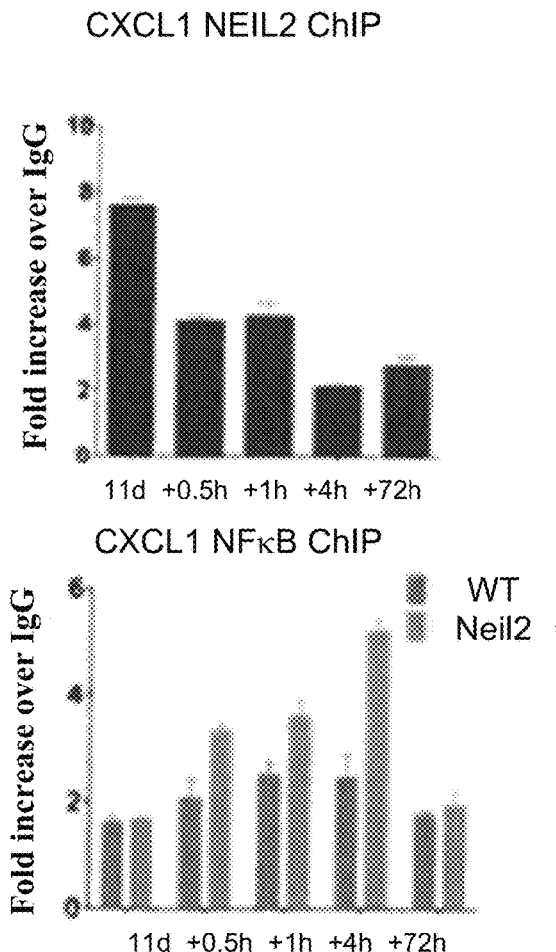

The Inventors have reported that RWPE and CDE stimulate CXCL1/CXCR2 pathway-linked innate neutrophil recruitment that in turn induces allergic sensitization and allergic airway inflammation (Hosoki et al., *The Journal of allergy and clinical immunology.* 2017; Hosoki et al. *American journal of respiratory cell and molecular biology.* 2016, 54(1):81-90; Hosoki et al., *The Journal of allergy and clinical immunology.* 2016; 137(5):1506-13 e2). In FIG. 2B, it is demonstrated that Neil2 KO mice show 5-fold greater CCL 11 expression. For these reasons, the initial focus of ChP experiments was on these two genes. WT and Neil2-null mice were subjected to a multiple CDE challenge model (FIG. 3A). ChTP analysis was performed using anti-NEIL2 or -NFkB Abs. qPCR amplification of the previously reported (Matsukura et al., *J Immunol.* 1999, 163(12):6876-83) proximal promoter region of NFkB-regulated CCL 11 (FIG. 3B) and CXCL1 (FIG. 3C) inflammatory chemokines surprisingly showed that NEIL2, normally remains bound to the promoter segment in these sensitized mice; however, its binding decreases upon allergen challenge. As expected, NFkB's binding to the identical segment was initially insignificant, but increased by an average of 1.5-3 fold at 30, 60 min and 4 h after CDE challenge, respectively, which closely parallels the extent of transcription of the corresponding genes. This increase was substantially higher in Neil2KO mice. Notably, intranasal administration of HIS-tagged recombinant NEIL2 (rNEIL2)+Chariot protein transfection reagent 1 h prior to CDE challenge reduced the recruitment of total inflammatory cells and eosinophils in bronchoalveolar lavage fluid, BALF. Western blots (WB) of lung lysates 72 h post-challenge confirmed the presence of HIS-tagged rNEIL2 in the lungs. These data suggest that NEIL2 binds to the promoter of NFkB-regulated CCL 11 and CXCL1, and administration of rNEIL2 to sensitized mice inhibits AIR.

The sites on the genome where NEIL2 binds after allergen challenge will be determined. Naive WT mice will be subjected to a RWPE/CDE single challenge model (SCM) (Hosoki et al., *The Journal of allergy and clinical immunology*. 2017; Hosoki et al., *Curr Opin Allergy Clin Immunol*. 2016, 16(1):45-50), or MGM (FIG. 3A), and euthanized at 20 min, 60 min, 4 h and 72 h after final RWPE/CDE challenge. The cross-linked extracted genomic DNA will be fragmented and immunoprecipitated with NEIL2 antibody and subjected to ChIP-seq analysis in the UTMB Next Generation Sequencing laboratory. PolyA+RNA at 4 h (peak of RNA transcription) will be subjected to RNAseq analysis. The results of ChIP-seq and RNA-seq will be compared to identify the transcriptome in each model where NEIL2 binds to its promoter site. The Inventors expect to identify a subset of the transcriptome where NEIL2 binds to the promoter regions in the MGM and stimulates AIR (72 h).

NEIL2's role in regulating NFkB- or STAT6-mediated gene transcription after allergen challenge will be elucidated. WT and Neil2KO mice will be subjected to in vivo experiments similar to those described above. The cross-linked genomic DNA will be immunoprecipitated with IgG, NFkB- or STAT6 antibodies, and subjected to ChIP-seq analysis. PolyA+RNA at 4 h will be subjected to RNAseq analysis. The results of ChIP-seq and RNA-seq will be compared to identify NEIL2-dependent NFkB- and STAT6 transcriptome in the single and MCMs. From these experiments, a set of 10 genes that are highly NEIL2-STAT6-dependent and 10 genes NEIL2-NFkB-dependent will be identified and validated by ChIP-PCR. WT mice, it is expected that the sites on the genome that are bound by NFkB and STAT6 will be a subset of the genes that bind NEIL2. Greater binding of STAT6 and NFkB in Neil2KO mice is expected. NEIL2's binding will decrease after CDE challenge, followed by a time-kinetic increase in STAT6 and NFkB recruitment.

The role of active site mutant in binding to specific regions of the genome after allergen challenge will be elucidated. It was previously reported that mutation of Lys49 in NEIL2, conserved among Nei orthologs, inactivates both base excision and AP lyase activities of NEIL2 (Bhakat et al., *Nucleic Acids Res.* 2004, 32(10):3033-9). WT HIS-tagged recombinant (r)NEIL2$^{WT}$ and active-site mutant (Lys49Arg) (Bhakat et al., *Nucleic Acids Res.* 2004, 32(10): 3033-9) HIS-tagged rNEIL2$^{ASM}$ will be transfected into Neil2KO mice and subjected to RWPE/CDE SCM and MGM. The crosslinked genomic DNA will be immunoprecipitated with anti-HIS antibody, and subjected to ChIP-PCR analysis. PolyA+RNA at 4 h (the peak of RNA transcription) will be subjected to RNAseq analysis. The results of ChIP-seq and RNA-seq will be compared to identify rNEIL2 vs. rNEIL2$^{ASM}$ dependent transcriptomes in each RWPE/CDE model, and their ability to convert the Neil2KO transcriptome to a WT transcriptome. The ability of rNEIL2$^{WT}$ vs. rNEIL2$^{ASM}$ to inhibit innate immune response (IIR) in SCM and AIR in MGM will be examined. It is expected that greater binding of rNEIL2$^{WT}$ than rNEIL2$^{ASM}$ to same genes as identified in studies described above. It is further expected that rNEIL2$^{WT}$ will demonstrate a greater ability to inhibit IIR and AIR than rNEIL2$^{ASM}$.

Figures 3D, 3E:
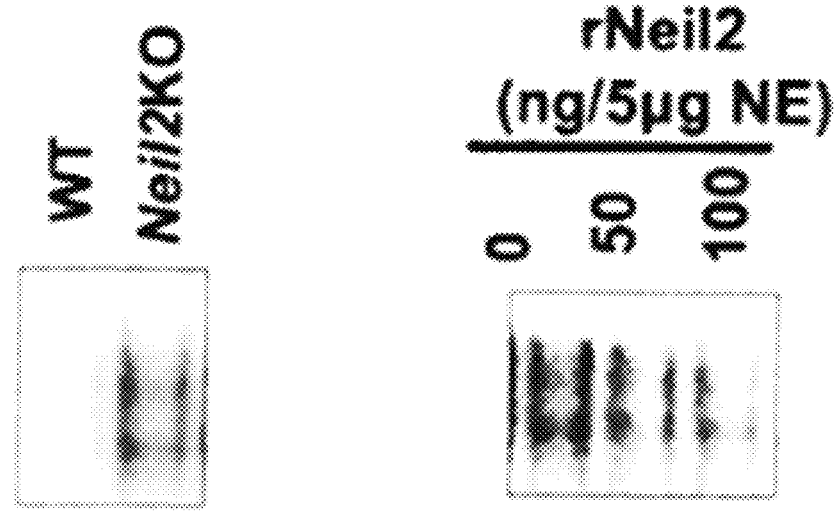
Figure 3F:
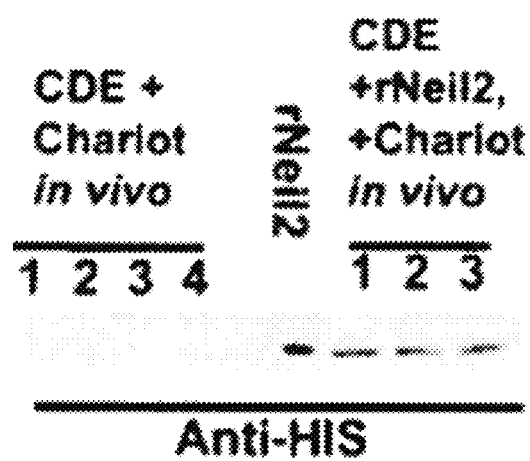
Figure 3H:
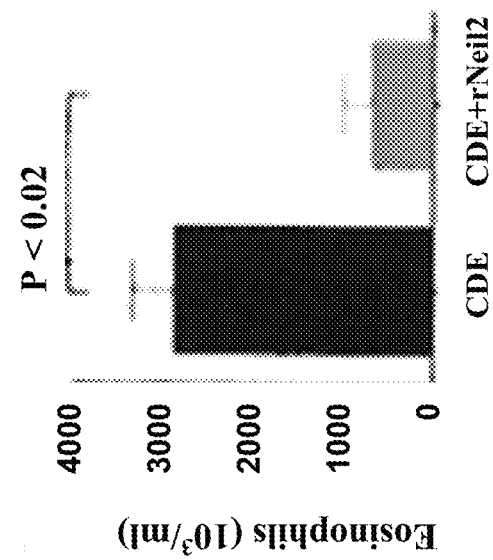
Figure 3G:
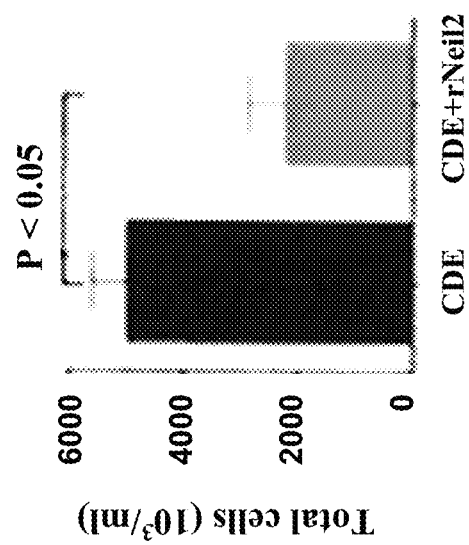

NEIL2 directly and selectively binds to NFkB and STAT6 sequence motifs. FIG. 2B demonstrates that Neil2 KO mice show 5-fold greater CCL 11 expression than WT mice in the CDE MCM. The ChIP data in FIG. 3B indicate that NEIL2 affects NFkB's binding of CCL 11 promoter. For these reasons, initial EMSA experiments were focused on the previously reported (Matsukura et al., *J Immunol*. 1999, 163(12):6876-83) proximal promoter region of NFkB-regulated CCL 11 using lung nuclear extracts (NEs) of the CDE MGM model (FIG. 3A). EMSA performed on lung NE from Neil2KO mice exposed to CDE MGM showed much higher DNA occupancy of NFkB p65-p50 than NEs from WT mice (FIG. 3D). Importantly, spiking the NEs with rNEIL2 induced a dose-dependent decrease in NFkB's binding, indicating that NEIL2 displaces/inhibits NFkB's binding to its cognate sequence (FIG. 3E). NEIL2 binds specifically to the NFkB motif in the context of different promoter sequences, and the binding is specific, as NEIL2 did not bind to mutant NFkB oligos (data not shown).

Experimental Design. DNA base modification within the promoter sequence can interfere with TF binding, resulting in dysregulation of transcription, which may interfere with proper cellular function. Studies will examine the binding of two TFs, NFkB and STAT6, both highly relevant to allergen-induced IIR and AIR (Kaplan et al., *Immunity*. 1996, 4(3): 313-9; Takeda et al., *Nature*. 1996, 380(6575):627-30; Yang et al., *The Journal of experimental medicine*. 1998, 188(9): 1739-50; Das et al., *Nature immunology*. 2001, 2(1):45-50), to their cognate motifs in the context of DNA base modification±NEIL2. Binding sites for those TFs are GC-rich, so the focus will be on modified bases such as 8-oxoG (guanine oxidation product), 5-OHC and 5-OHU (cytosine oxidation products). Their effects on TFs binding and NEIL2-mediated modulation therein will be examined as follows. Based on structural and DNA-protein interaction analysis of NFkB, oligos will be designed (promoter sequence of CCL 11 encompassing NFkB) with site-specific 8-oxoG or 5-OHC or 5-OHU in the corresponding position of G or C, respectively, and perform EMSA using NEs from lungs of RWPE/CDE-treated SCM and MCM, and nasal curette samples NC and AR human subjects before pollen season and at peak of pollen season, and purified STAT6 or NFkB±purified rNEIL2$^{WT}$ or rNEIL2$^{ASM}$.

It is contemplated that purified NEIL2's binding to the damage-containing oligo within the NFkB or STAT6 motif will be significantly higher; by contrast, purified NFkB or STAT6 binding will be weak or they may not bind at all. The Inventors contemplate that NFkB or STAT6 will stimulate NEIL2-mediated BER of the oxidized base to allow binding of NFkB or STAT6 for gene transcription. It is expected that NE of sensitized mice and humans will elicit greater binding to sequence motifs than non-sensitized mice and humans, and rNEIL2$^{WT}$ but not rNEIL2$^{ASM}$ should be able to reverse this binding.

Figure 6:
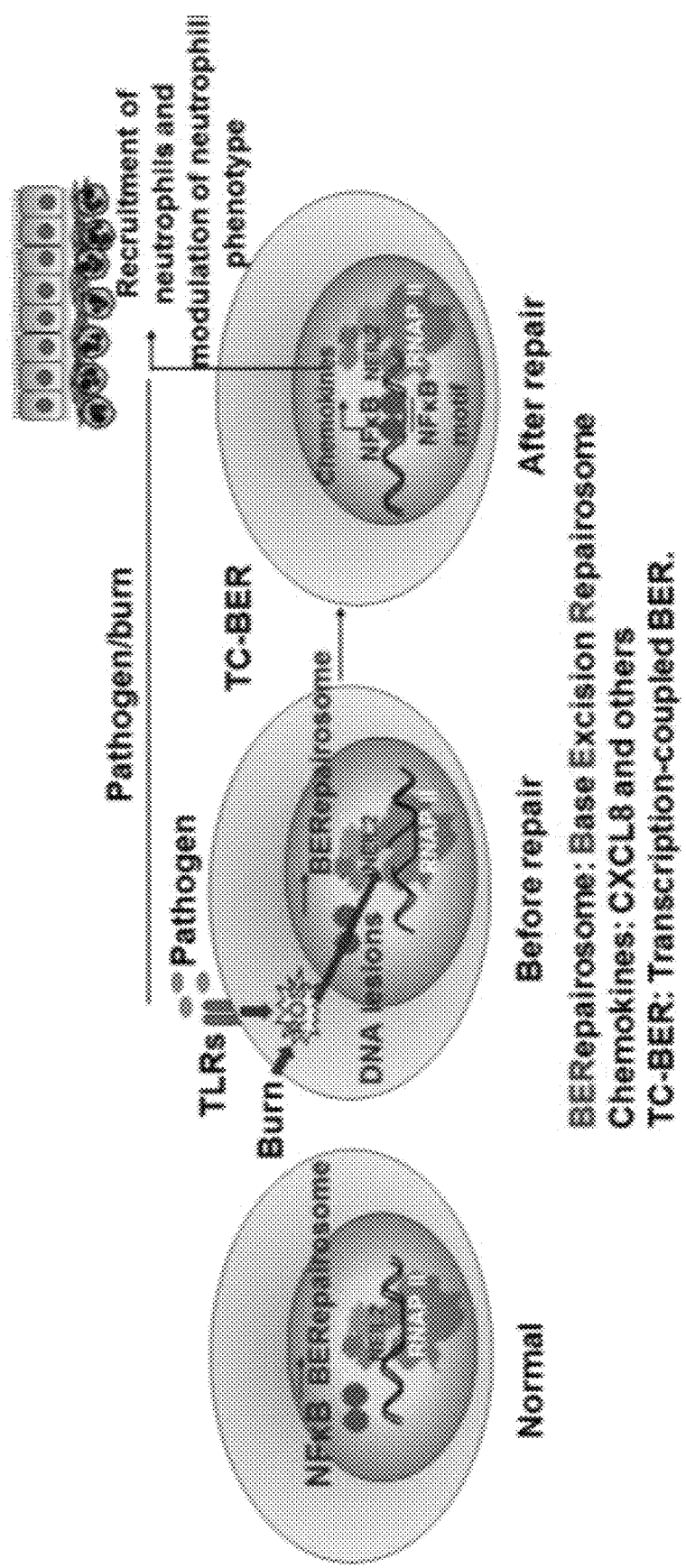
FIG. 6. A schematic showing the relationship between chemokine CXCL8, NFkB pathway, transcription-coupled (TC)-BER, neutrophil recruitment and activation, and disease.

The biological role of NEIL2 in the STING complex. Signal transduction, protein trafficking, protein degradation, various DNA-protein transactions, and many other cellular processes are all accomplished by dynamic protein complexes, often temporally assembled and disassembled for a specific purpose. Identifying the proteins in the complex and characterizing their dynamic interactions should help elucidate the sequential steps and their mechanisms. NEIL2 has a well-established role in the nucleus for repairing oxidized DNA bases. NEIL2 has also been detected in the cytoplasm by cell fractionation; however, no function has been assigned to cytoplasmic NEIL2 prior to these studies. As NEIL2 inhibits (FIG. 2) and STING stimulates CDE-induced IIR and AIR, it was postulated that NEIL2's cytoplasmic role is to limit the STING-mediated inflammatory signaling pathway and so maintain cellular homeostasis. A striking difference was found between the protein-protein interactions of NEIL2 in lungs of non-sensitized CDE SCM (FIG. 4A) vs. sensitized MCM (FIG. 4B). There is no detectible complexing of NEIL2 with IRF3 and STING in the SCM (FIG. 4A). By contrast, in the MCM, NEIL2 complexes with IRF3 and STING (FIG. 4B), but not with PNKP (data not shown), a known NEIL2-associated protein in the nucleus (Chakraborty et al., *The Journal of biological chemistry*. 2015, 290(41):24636-48). The absence of PNKP interactions not only demonstrates the specificity of the complex formation in the cytoplasm, but also indicates that total repair of extruded DNA fragments from the nucleus is not necessary, as other proteins necessary for repair completion are absent in the cytoplasmic NEIL2 complex. Most interestingly, the stable association of NEIL2 with the STING complex in sensitized mice persisted for at least 7 days after the 5th challenge (FIG. 6B). This association was dependent on the presence of a DNA template in the cytosol, because DNAse treatment abolished the association (FIG. 4B, bottom, STING+DNAse). To further establish whether NEIL2 acts as an anti-inflammatory factor, NFκB and STAT6 translocation to the nucleus were monitored in response to CDE. In the CDE SCM, there was no significant change in the levels of Neil2, NFκB or STAT6 in the nucleus (FIG. 4C). By contrast, in the CDE MCM, the final CDE challenge significantly decreased NEIL2's nuclear level by 4 h, whereas NFkB peaked at 4 h and STAT6 by 1 h (FIG. 4D). Furthermore, in the MCM, pSTAT6 disappeared from the nucleus by 4 h in WT mice; by contrast, it persisted at 4 h in Neil2KO mice (FIG. 4E).

Determine the role of NEIL2 in formation of an active STING complex. Cytosolic extracts of lungs from WT and Neil2KO mice subjected to RWPE/CDE SCM and MCM and challenged with either PBS or RWPE/CDE, and nasal curette samples from NC and AR subjects before pollen season at peak of pollen season will be examined. The STING-associated proteins (TBK1 and IRF3) in the STING complex will be examined by IP with anti-STING antibody, and probed for IRF-3, TBK1. The biological function of the STING complex will be determined by quantifying total levels of pTBK1, pIRF3, NFκB and pSTAT6 in cytosol and nuclear extracts, and the levels of 84 Type I IFN genes and 84 AIR genes by PCR array (SA biosciences). Because chronic oxidative stress in allergic mice and AR humans is likely to generate SSODDF required as a platform for formation of the Neil2-STING complex, the investigators expect to see association between NEIL2 and STING in allergic (MCM in mice and AR humans), but not SCM in mice and NC humans. Furthermore, compared to WT mice, the investigators expect greatly increased pSTING, pIRF3 activation in Neil2KO mice.

Determine the role STING in NEIL2-mediated activation of IRF3. WT, StingKO will be subjected to RWPE/CDE SCM and MCM followed by a final challenge with either PBS or CDE. The NEIL2-IRF3 complex will be examined by IP with anti-NEIL2 antibody, and probed for IRF-3, TBK1 in lung cytosol. The biological function of the IRF3 complex will be elucidated kinetically as above. Compared to WT MCM, the investigators expect greatly reduced pTBK1, pIRF3, NFκB and pSTAT6 in lung cytosol and NEs, and Type I IFN and AIR genes in StingKO MCM. Furthermore, in WT mice, greater STING-activation is expected in MCM than SCM.

Elucidate the role of active site mutant of NEIL2 in formation of an active STING complex. $(r)NEIL2^{WT}$ and $rNEIL2^{ASM}$ will be transfected into Neil2KO mice and subjected to the RWPE/CDE SCM and MCM. The same readouts as above will be performed. $(r)NEIL2^{WT}$, but not $rNEIL2^{ASM}$ is expected to stimulate NEIL2-STING complex formation and inhibit CDE-induced AIR.

Figure 5A:
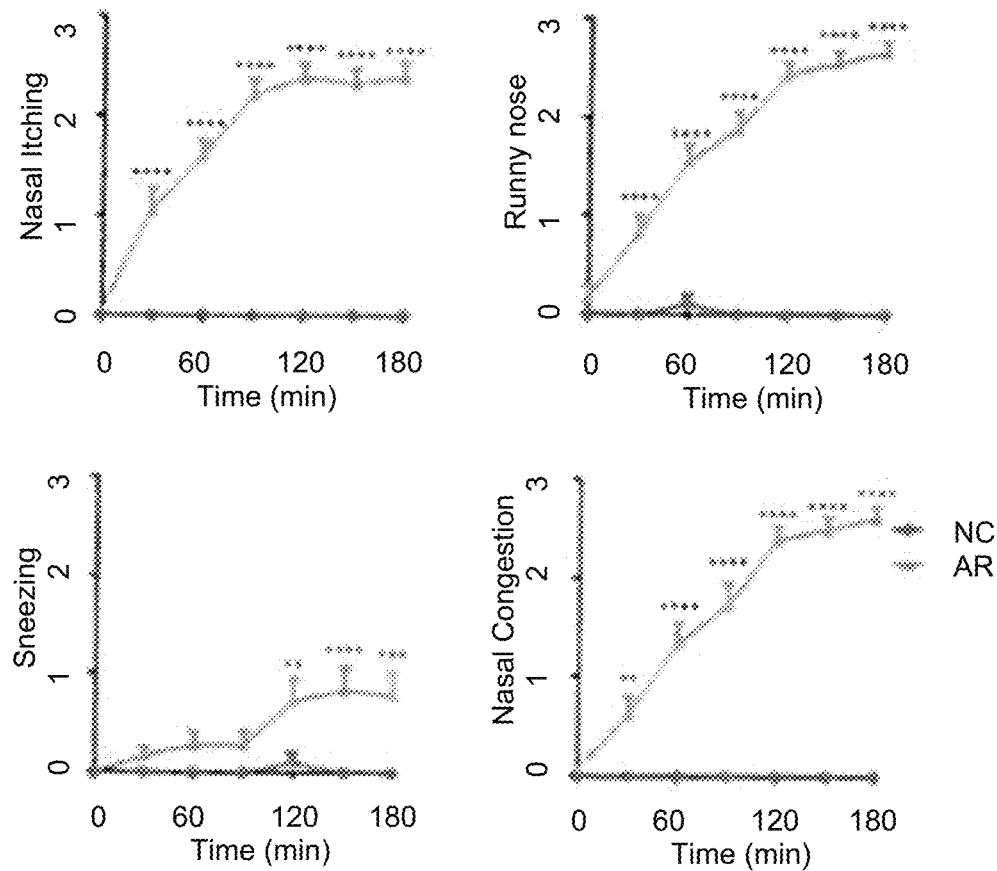
FIGS. 5A-C. RWP exposure of healthy and ragweed-allergic subjects in BRC-PEC. Ragweed-allergic subjects (AR, n=18) and normal control (NC) subjects (NC, n=10) were exposed to RWP.
Figure 5B:
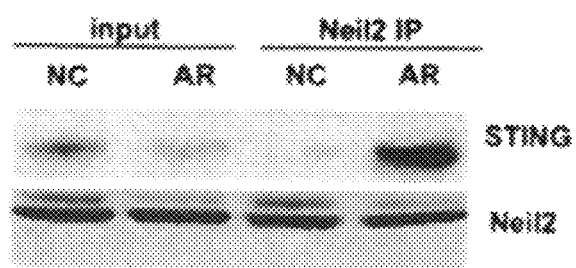
Figure 5C:
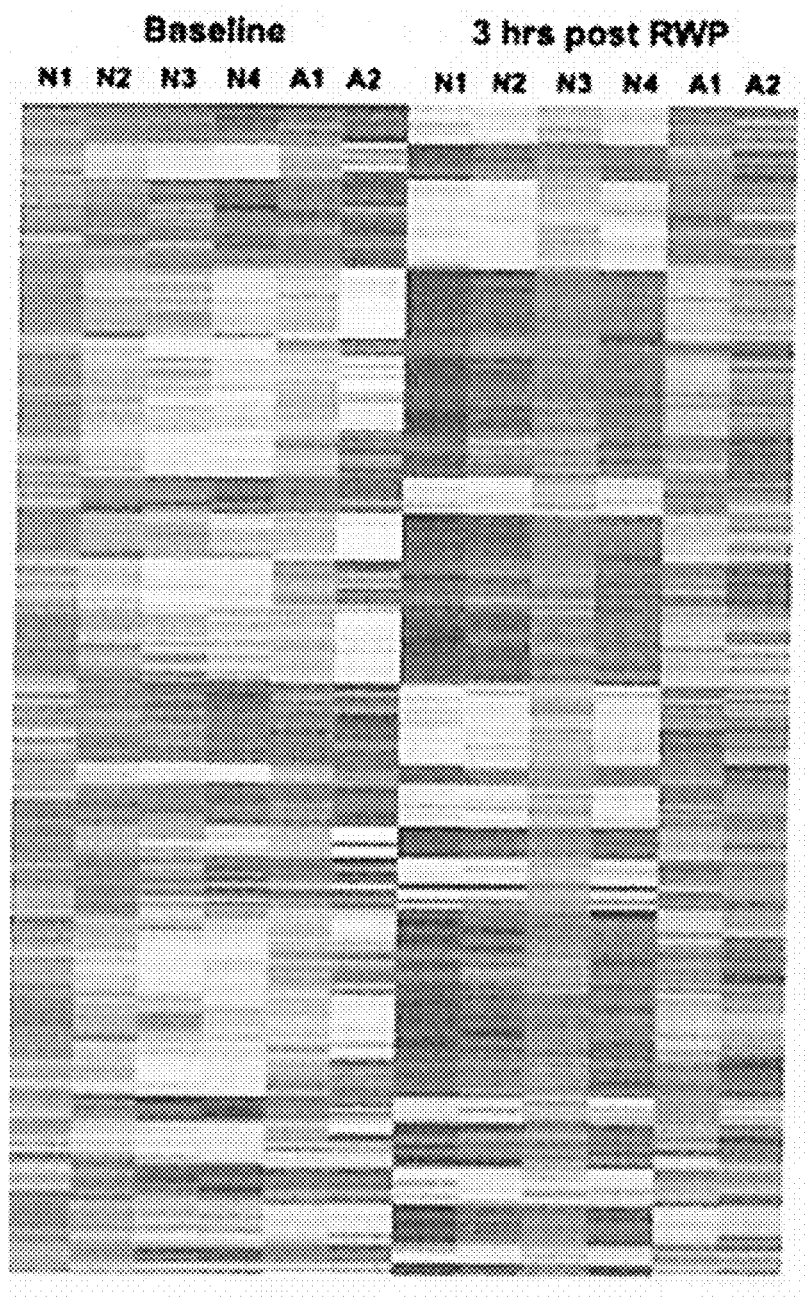

The investigators performed a preliminary study at the PEC to determine reproducible of results. Exposure of AR (n=18) but not NC subjects (n=10) to defatted RWP grains increased the total nasal symptom score (TNSS) in 30 mins (FIG. 5A). Compared to baseline z score values for gene expression in nasal curette samples measured by RNA-seq analysis in four NC subjects (N1-N4), RWP exposure for 3 hrs induced clear changes in –1100 genes (FIG. 5B). The two AR subjects (A1, A2) seemed to have a distinct gene response compared to healthy subjects. Nasal curette samples from an NC subject and an AR subject were subjected to NEIL2 IP and STING WB. Even though the NC had slightly greater input STING, the amount of STING that was IP'd with NEIL2 was much greater in AR than NC (FIG. 5C).

III. Treatment of Bacterial Infections

The rapid emergence of antibiotic resistant bacteria is occurring worldwide, and thus bacterial infections have become a real threat to our society. Many of these bacteria are already responsible for placing a substantial clinical and financial burden on the global as well U.S. health care system, patients, and their families. The crisis for developing bacterial resistance has been attributed to the overuse and misuse of various antibiotics, as well as a lack of development of new drug by the pharmaceutical industry due to a variety of reasons. Coordinated research efforts and new way of thinking are greatly needed to combat such untreatable organisms.

The World Health Organization (WHO) lists 12 bacterial genera that are in the WHO priority pathogen list for R&D for new antibiotics. (available on the workd wide web at URL who.int/medicines/publications/WHO-PPL-Short_Summary_25Feb-ET_NM_WHO.pdf), *Klebsiella pneumoniae* (Kp) is on this priority list. It causes life-threatening infections, particularly in susceptible and immuno-compromised individuals. The general strategy used to fight high risk pathogens is use of antibiotics to which the bacteria is not resistant, reduce exposure, and is some situations, use vaccines or monoclonal antibodies. Here it is shown that delivering a recombinant NEIL2 biologic into the lungs of the host as a paradigm-shifting strategy to reduce damage to the transcribed genome in the lungs; the lungs are able to accurately mount the innate immune response that is required to protect the host from fatality induced by lethal doses of a WHO priority list of pathogens.

As a proof-of principal, the Inventors have developed Kp-infected animal model, and these animals die within 3 days of infection. Because of the emergence of multidrug resistance and tolerance, it is important to better understand the mechanisms and/or develop alternative strategy to combat such untreatable organisms. Severe bacterial infections induce DNA damage in the tissues, thus profoundly affecting the host's ability to mount an innate immune response required to destroy the pathogen. One way to fight the infection should be to correct the host's ability to repair its DNA accurately. The inventors investigated one such biologic, recombinant NEIL2 (rNEIL2), a DNA repair protein. It has been shown that intracellular administration of rNEIL2 with a peptide carrier introduces rNEIL2 into the lung cells and increases survival to >60% against lethal *Klebsiella pneumoniae* infection 14 days after infection in mice.

Reactive oxygen species (ROS), generated endogenously under normal physiological conditions, and/or due to cellular responses to various xenobiotics, cytokines, and bacterial infection, target cellular macromolecules, including the genomic DNA. However, organisms are equipped with an arsenal of DNA repair proteins that continuously maintain genome's integrity for species survival. ROS-induced oxidized DNA bases are primarily repaired via the base excision repair pathway, which is initiated with excision of the oxidized bases by a family of enzymes, called DNA glycosylases. NEIL2 has been cloned and is involved in mammalian DNA-base excision repair. Neil2-null mice are extremely susceptible to oxidative stress.

Bacterial infection induces severe inflammatory response which in turn can induce genome damage due to oxygen free radicals. The resultant accumulation of damage in the transcribed sequences can be lethal to the cells. The inventors contemplate that NEIL2 first repairs the oxidized DNA bases within the promoter regions and exons in the actively transcribing genes of innate immune response genes, and subsequently provides regulatory control of expression of those genes via interplay with NFκB. It is further contemplated that the coordinated action of these two NEIL2-dependent processes is responsible for maintaining the fidelity of a precise cassette of chemokines and will provide protective function against bacterial infection. This is a paradigm shift, and to the best of our knowledge, the first example of maintaining genomic integrity of the host provides protection from an infection with a lethal pathogen.

Role of NEIL2 and neutrophil function. Preliminary studies indicate that NEL2 regulates the NFκB-mediated pro-inflammatory response and that intrapulmonary delivery of NEIL2 protects mice against lethal bacterial infection. Both infection and smoke inhalation-related injuries in ARDS patients can result in genome damage due to oxygen free radicals. The resultant accumulation of damage in the transcribed sequences can be lethal to the cells. The Inventors propose that NEIL2 first repairs the oxidized DNA bases within the promoter regions and exons in the actively transcribing genes of neutrophil-activating chemokines, and subsequently provides regulatory control of expression of those genes via interplay with NFκB. It is further proposed that the coordinated action of these two NEIL2-dependent processes is responsible for the synthesis of a precise cassette of chemokines, including CXCL8 that defines the protective neutrophil phenotypes against ARDS.

Figure 9B:
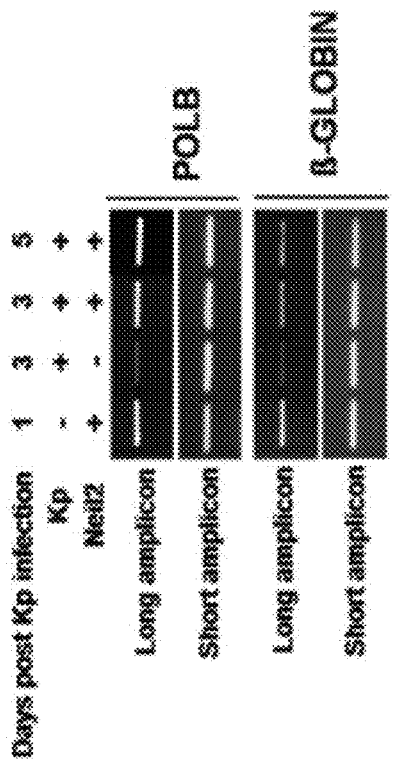
FIGS. 9A-D.
Figure 9A:
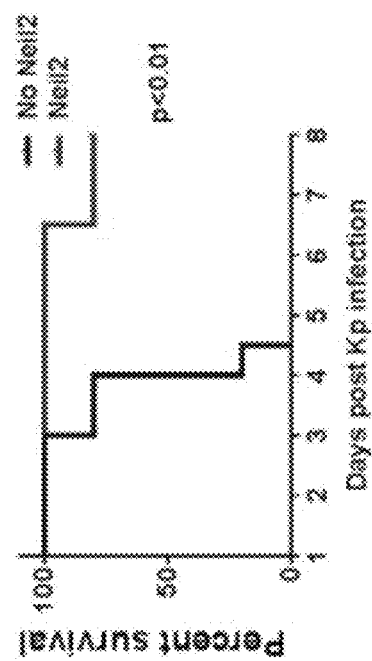
Figure 9D:
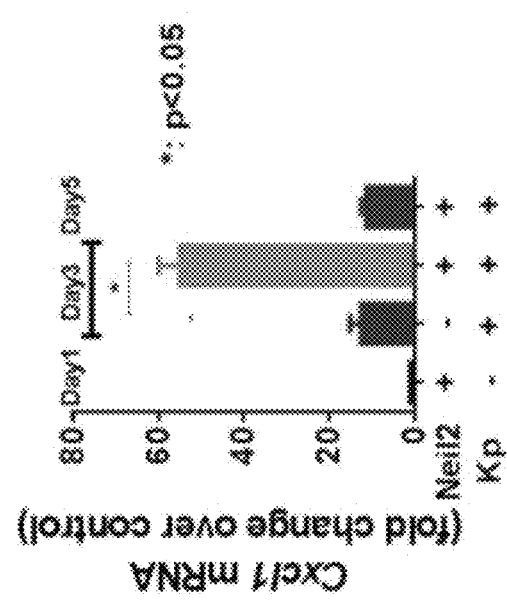
Figure 9C:
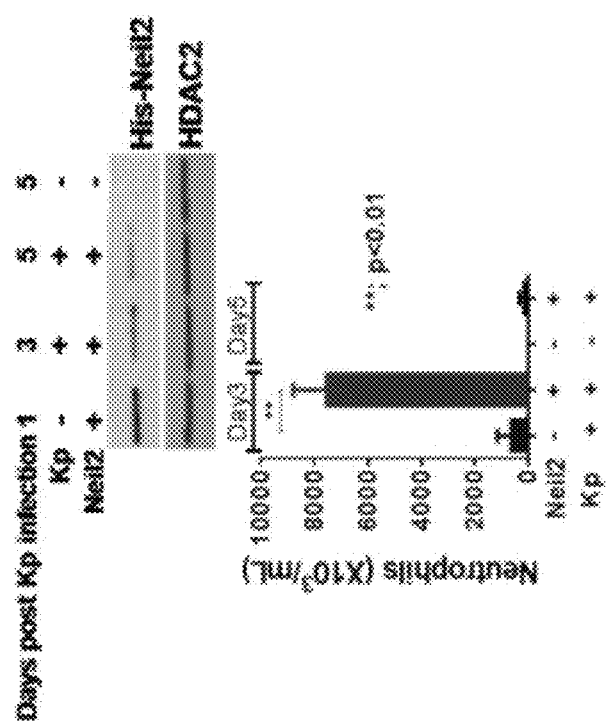
Figure 10:
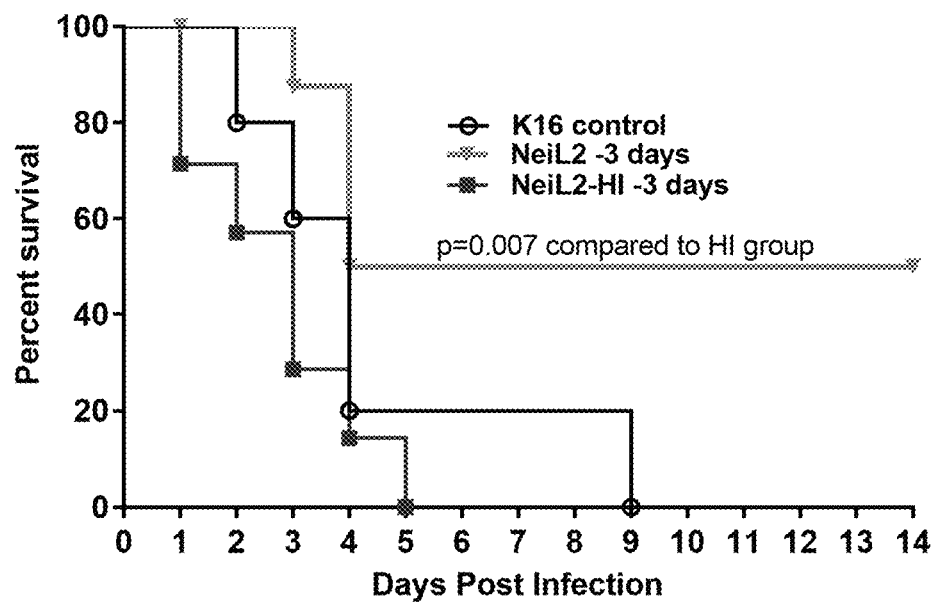
FIG. 10. Protective effect of NeiL2 on mice intranasally infected with *Klebsiella pneumoniae*. C57Bl/6 mice (n=5-8) were pre-treated with either K16 control peptide or native NeiL2 or heat-inactivated (HI) NeiL2 3 days before intranasal infection with $2.4 \times 10^5$ CFU *K. pneumoniae*. Animal survival was monitored and recorded for 14 days.
Figure 11:
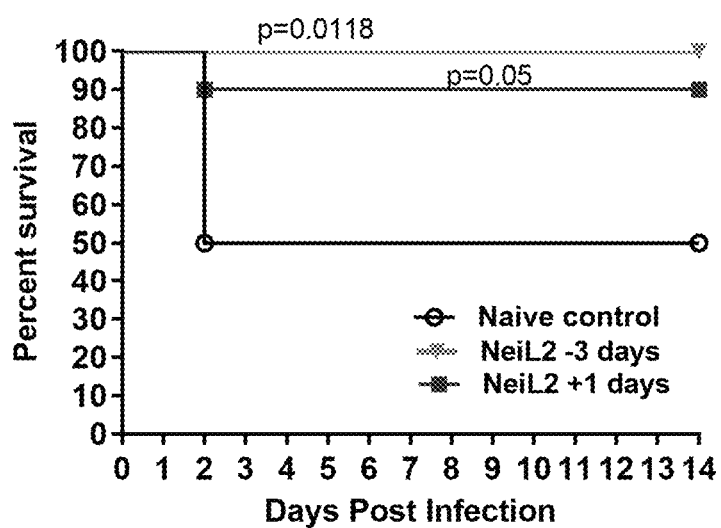
FIG. 11. Protective effect of NeiL2 on mice intranasally infected with *Acinetobacter baumannii*. C57bl/6 mice (n=10) were intranasally infected with $7.0 \times 10^8$ CFU of pan-drug resistant *A. baumannii* and treated with NeiL2 either 3 days before or 1 day after the infection. Untreated mice served as control. Animal survival was monitored and recorded for 14 days.

Non-human primate (NHP) model. Knowledge of neutrophil recruitment and its phenotype during the time course from initial infection to resolution or death is lacking for human patients. Use of NHPs for such studies can fill this missing gap. Certain aspects focus on the Tier-1 select agent *Yersinia pestis* that leads to deadly pneumonic infection followed by sepsis and multi-organ failure (Perry and Fetherston, *Clin Microbiol Rev* 1997, 10:35-66; Kwit et al., 2015. Human Plague United States, 2015, vol 64, p 918-919. Centers for Disease Control and Prevention). Recent studies showed how a protective investigational vaccine recruits neutrophils that clear the pathogen in mice and rats (Tiner et al., *Infect. Immun.* 2015, 83:1318-1338; Tiner et al., *Clin Vaccine Immunol.* 2015, 22: 1255-1268; Tiner et al., *NPJ Vaccines* 2016, 1:16020).

Characterization of NEIL2 in relation to ARDS and bacterial infection. Acute respiratory distress syndrome (ARDS) is a common life threatening condition with mortality as high as 40%. Disease onset is rapid and progressive and is usually the result of direct insult to the lung caused by sepsis, pneumonia, or sterile injuries such as from burn and smoke inhalation. Neutrophil recruitment and its dysregulated activation are hallmarks of ARDS. The chemokine CXCL8 plays a prominent role in recruiting neutrophils and activating their effector function in infected/injured tissue. Neutrophils adopt different functional phenotypes, which are dictated by its interactions in the blood and tissue. CXCL8-mediated microbial killing or repair sets the stage for subsequent phenotypical changes in the neutrophils that lead to its clearance in the infected tissue and resolution.

The Inventors recently made a novel observation that NETL2, a DNA glycosylase involved in repair of oxidized bases via transcription-coupled base excision repair (TC-BER), plays an important role in innate immunity. The Inventors observed that it inhibits NFkB-mediated neutrophilic lung inflammation and that administering NEIL2 protects mice against lethal bacterial pneumonia. The NFkB signaling pathway plays an important role in CXCL8 production, indicating that events downstream of NEIL2-mediated and CXCL8-associated activity define the neutrophil phenotype. The Inventors contemplate that neutrophil phenotypes defined by the coordinated action of CXCL8-CXCR1/CXCR2 and NEIL-2-BER-NFκB axes determine immune functions that successfully resolve inflammation, and a dysregulation in these interactions results in ARDS.

The studies described below will (i) determine the roles of CXCL8 and neutrophil phenotype in ARDS by characterizing blood and bronchoalveolar lavage fluid (BALF) neutrophil phenotypes; (ii) define the relationship between CXCL8 levels, neutrophil phenotype, and severity of infection in a non-human primate (NHP) ARDS model; and (iii) determine the roles of NEIL2 and neutrophil phenotype in ARDS.

Determine the roles of NEIL2 in ARDS. Pathogenic bacterial infection and severe burn/smoke-inhalation result in an extensive amount of oxidative damage to the genome resulting from Reactive Oxygen Species (ROS) producing a massive systemic inflammation that could lead to ARDS (Hazra et al., *J. Biol Chem.* 2002, 277(34):30417-20; Cuevas-Ramos et al., *PNAS.* 2010, 107:11537-11542; Wu et al., *Infect Immun.* 2011, 79:75-87; Koeppel et al., *Cell Rep.* 2015, 11:1703-13; Purschke et al., *J Invest Dermatol.* 2010, 130: 86-92; Xu et al., *Clin Exp Pharmacol Physiol.* 2016, 43: 921-929). At this time, very little is known regarding the mechanistic link between oxidative DNA damage and ARDS. The DNA glycosylase NEIL2 has been cloned and characterized, and reported the sequential events by which it repairs oxidatively damaged bases via the BER pathway (Hazra et al., *J. Biol Chem.* 2002, 277(34):30417-20; Chakraborty et al., *J. Biol Chem.* 2015, 290:24636-24648). Most importantly, it was shown for the first time, both in vitro biochemically and in vivo using a Neil2-null animal model, that NEIL2 preferentially repairs the oxidized bases from the transcribed genome via the transcription-coupled BER (TC-BER) pathway. Furthermore, the inventors also made an exciting observation that NEIL2 regulates neutrophilic inflammation, indicating its multifunctional roles.

Does preventing oxidative DNA damage by NEIL2 skew neutrophil phenotype in a NHP model of plague? The Inventors observed that intracellular delivery of rNEIL2 into the lungs of mice provided strong protection against mortality in the *Klebsiella pneumoniae* (Kp) mediated pathogenic infection (FIG. 9A). Replicating bacteria trigger the TLR receptors and dysregulated neutrophil activation, and this is turn, stimulates progressively increasing ROS-generation that can damage the genome (Huang et al., *Am J Respir Cell Mol Biol.* 2013, 49: 798-807). Thus, a crucial component of the host immune response to robust bacterial infection must induce TC-BER of the pro-inflammatory genes such as CXCL8 that stimulates neutrophilic inflammation. Given there is DNA damage accumulation in pathogenic infection, the Investigators assessed the DNA damage accumulation in POLB and 13-Globin genes, highly transcribing genes in the mouse lungs (Enkhbaatar et al., *Lancet.* 2016, 388:1437-1446) by LA-qPCR (FIG. 9B). Indeed, a significant amount of oxidative genome damage was observed after Kp infection, however, intranasal delivery of rNEIL2 (FIG. 9C, upper panel), prior to bacterial infection, efficiently repaired the transcribed genome (FIG. 9B; lanes 3, 4). This led to the recruitment of neutrophils (FIG. 9C, lower panel) in response to elevated CXCL1 levels (FIG. 9D) that could clear the bacterial load leading to reduced animal mortality.

Based on observations of NEIL2's protective role against pathogenic pneumonic infection in mice, the outcome of nebulization-mediated intracellular delivery of recombinant NEIL2 via engineered non-covalent peptide K16SP in NHPs pre- and post-lethal doses of aerosolized *Y. pestis* will be tested. If we find any protective function in terms of survival compared to control group, bronchial brushings from the NHPs will be assessed before and after NEIL2 administration/*Y. pestis* infection (day 2) to monitor the DNA damage and immune response following the above mentioned studies. Assays described above will be performed here as well. In addition, the bacterial load in BALF will be monitored at these time points to assess NEIL2's role in clearance of infection by examining the bacterial burden. The pathology in the lungs, spleen, and liver of surviving animals at the time of euthanization will be determined. In addition, the lung architecture will be examined by CT scans at appropriate time points. These experiments will be coordinated with other studies.

Statistical analysis. For these studies, statistical significance will be determined using two-sided unpaired Student's t-test. Significance will be evaluated at the level $P>0.05$ (NS), $*P<0.05$, $P<0.01$ and $*P<0.005$.

The time course-based observations of DNA damage and neutrophilic response in the NHP model are expected to demonstrate NEIL2's therapeutic potential to reduce ARDS-related and other bacterial infection related symptoms by alleviating oxidative genome damage and lung injury.

IV. NEIL2 as a TNF-Antagonist

TNF antagonists are indicated for Rheumatoid arthritis, juvenile idiopathic arthritis, psoriatic arthritis, ankylosing spondylitis, plaque psoriasis, pediatric plaque psoriasis, axial spondyloarthritis, Crohn's disease, pediatric Crohn's disease, ulcerative colitis and a growing body of other diseases. Here we propose that recombinant NEIL2 delivered to local tissues with the aid of a peptide can serve as an inhibitor of TNF in these and other diseases. Local deliver has the advantage that local TNF will be inhibited, thereby reducing toxicity associated with systemically delivered TNF antagonist biologics.

Figures 7A, 7B:
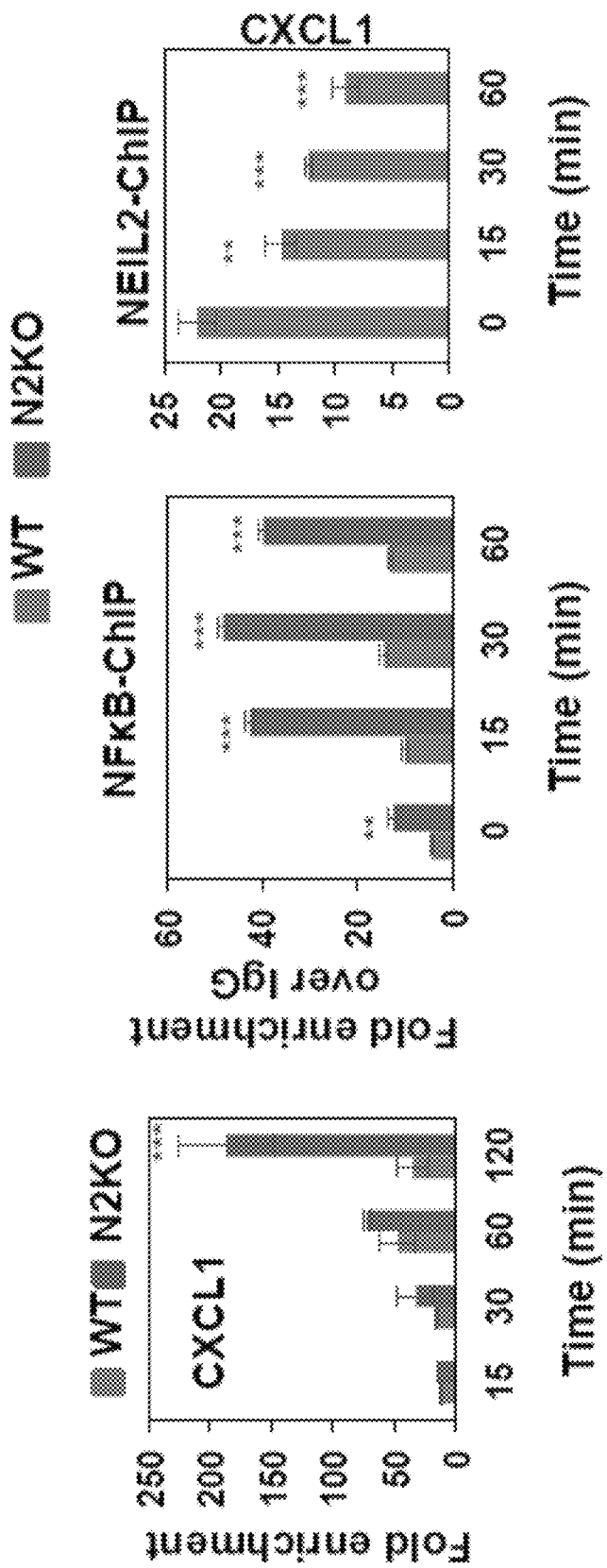
FIGS. 7A-B.

Tumor necrosis factor-alpha (TNF-α) is a potent pro-inflammatory cytokine and also a central regulator of inflammation. TNF-α plays a critical role in host defense. It is the first cytokine that appears in the blood stream after any infection, injury or stress, and thereby acts as body's danger detection system. However, chronic inflammation-induced TNF-α release in the system is not good for the body. It induces an innate inflammatory response and thus plays an important pathogenic role. In such cases, TNF-α antagonists have been considered as an effective therapeutic option for treating various inflammatory disorders. TNFα challenge stimulated greater upregulation of CXCL1 and other several pro-inflammatory genes (not shown) in Neil2-null than WT mice (FIG. 7A). As these genes are NFκB-regulated, the association of NFκB in the promoter region of these genes was examined by ChTP analysis following mock/TNFα challenge at indicated time points by quantitative ChTP (qChIP) using oligos spanning NFκB cognate sequences (FIG. 7B). NFκB's binding was insignificant in mock-treated mouse lungs. TNFα-treatment significantly increased the association of NFκB with gene promoters, particularly in Neil2-null mice. By contrast, NEIL2's occupancy with those promoters was strong in mock-treated mouse lungs and showed a time-dependent gradual decrease after TNFα treatment. This clearly indicates that NEIL2's occupancy of the NFκB cognate binding sites in the promoters of pro-inflammatory genes regulates NFκB-mediated neutrophilic inflammation.

Recombinant proteins are now widely used as therapeutic agents for various diseases. Several engineered non-covalent peptide carriers for targeted delivery of histidine (His)-tagged rNEIL2 to mouse lungs were screened and an engineered peptide carrier was identified (designated K16SP) (Sarkar et al., *PLoS One.* 2014, 9(5):e97655), that delivered the highest amount of rNEIL2 protein to the mouse lungs (FIG. 8A). rNEIL2 was retained in the lungs for at least 3 days (FIG. 8B), reduced NFκB binding to the cognate sequences of mouse CXCL1 promoter in the lung nuclear extracts (FIG. 8C), and significantly reduced TNFα-induced neutrophil recruitment in lungs (FIG. 8D). Hence, targeting of rNEIL2 may be used as a therapeutic interventions in lung inflammation.

V. Pharmaceutical Formulations and Administration

Certain embodiments include compositions including rNEIL2 or a variant thereof with one or more of the following: a pharmaceutically acceptable diluent; a carrier; a solubilizer; an emulsifier; and/or a preservative. Thus, the use of one or more rNEIL2 agent described herein in the preparation of a pharmaceutical composition of a medicament is also included. Such compositions can be used in the treatment of allergic asthma, allergic rhinitis, or bacterial infections.

The therapeutic agent(s) may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the therapeutic agent(s) that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from at least, at most, or about 4.0 to at least, at most, or about 8.5, or alternatively, between at least, at most, or about 5.0 to 8.0, including all values and ranges there between. Pharmaceutical compositions can comprise TRIS buffer of at least, at most, or about a pH of 6.5-8.5, including all values and ranges there between, or acetate buffer of at least, at most, or about a pH of 4.0-5.5, including all values and ranges there between, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and/or reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, inhalation, instillation, intravenous, intraperitoneal, oral, intralymphatic, subcutaneous administration, intraarterial, intramuscular, intrapleural, intrathecal, and by perfusion through a regional catheter.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258, 6,794,357, 6,737,045, and 6,488,953, all of which are incorporated by reference. According to certain aspects, at least one therapeutic composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one therapeutic composition is delivered in a particle size effective for reaching the lower airways of the lung or sinuses. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

All such inhalation devices can be used for the administration of a therapeutic composition in an aerosol. Such aerosols may comprise either solutions (both aqueous and non-aqueous) or solid particles. Metered dose inhalers typically use a propellant gas and require actuation during inspiration. Dry powder inhalers use breath-actuation of a mixed powder. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a therapeutic composition described herein.

Once the therapeutic compositions have been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, at least, at most, or about 0.1% to at least, at most, or about 0.5% (w/v). Surfactant stabilizers, such as TWEEN®-20 or TWEEN®-80 (ICI Americas, Inc., Bridgewater, N.J., USA), may also be added in conventional amounts.

The components used to formulate the therapeutic compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents. Compositions for parental or pulmonary administration are also sterile, substantially isotonic and made under GMP conditions.

For the compounds described herein, alone or as part of a pharmaceutical composition, such doses are between at least, at most, or about 0.001 mg/kg and 10 mg/kg body weight, preferably between at least, at most, or about 1 and 5 mg/kg body weight, most preferably between 0.5 and 1 mg/kg body weight, including all values and ranges there between.

Therapeutically effective doses will be easily determined by one of skill in the art and will depend on the severity and course of the disease, the patient's health and response to treatment, the patient's age, weight, height, sex, previous medical history and the judgment of the treating physician.

Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

In another embodiments the therapeutic compositions can be used as an anti-bacterial polypeptide composition. The prevalence of antibiotic and/or drug resistance in bacteria is becoming one of the leading public health threats. Current antibiotics interfere with the critical biological processes of the pathogens and cause death or growth arrest of the bacteria. As a result, antibiotic therapy exerts a strong selective pressure to favor emergence of antibiotic resistant strains. For that reason, the number of bacteria strains that are resistant to front-line antibiotics is growing at an alarming rate, yet there are no signs of replacement treatments in the market or pipeline. The few alternatives that do exist are either expensive, highly toxic, and/or slow acting. Resistance is even growing among infections that today are considered easily treatable, such as tuberculosis, *Salmonella, E. coli*, and gonorrhea.

In some embodiments a polypeptide composition can be used for treating and/or preventing a bacterial infection, such as *Acinetobacter baumannii, Bacillus cereus, Bacillus anthracis, Clostridium botulinum, Clostridium difficile, Clostridium tetani, Clostridium perfringens, Corynebacteria diphtheriae, Enterococcus* (e.g., *Streptococcus* D), *Listeria monocytogenes*, Pneumoccoccal infections (e.g., *Streptococcus pneumoniae*), Staphylococcal infections and Streptococcal infections; Gram Negative bacteria including *Bacteroides, Bordetella pertussis, Brucella, Campylobacter* infections, enterohaemorrhagic *Escherichia coli* (EHEC/*E. coli* O157:H7) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholerae* and *Yersinia*; acid fast bacteria including *Mycobacterium tuberculosis, Mycobacterium avium-intracellulare, Myobacterium johnei, Mycobacterium leprae*, atypical bacteria, *Chlamydia, Mycoplasma, Rickettsia*, Spirochetes, *Treponema pallidum, Borrelia recurrentis, Borrelia burgdorfii* and *Leptospira icterohemorrhagiae* and other miscellaneous bacteria, including *Actinomyces* and *Nocardia*.

Resistant pathogens are especially prevalent in hospitals. Especially dangerous strains such as methicillin-resistant *Staphylococcus aureus* (MRSA). In certain aspects the polypeptide compositions can be used to treat several healthcare associated (HA) and community associated (CA) strains. HA and CA strains include, but are not limited to ST228, ST239, ST5, ST22, ST45, ST240, ST247, ST250, ST15, ST30, ST36, ST579, ST45, ST59, ST80, ST1:USA400, and ST8:USA300.

Infections caused by certain microorganisms, such as certain gram-negative bacteria are generally unresponsive to present-day antibiotics due to the inability for medicines to penetrate their thicker cell walls. Certain acid-fast bacilli including *Mycobacterium tuberculosis* have also become multi-drug resistant.

The antibacterial compositions can be formulated for administration/use via any suitable route, including but not limited to orally, parentally, by inhalation, rectally, or topically in dosage unit formulations containing conventional pharmaceutically acceptable carriers, adjuvants, and vehicles. In preferred embodiments, the compositions are formulated for administration/use as an inhalant.

Certain aspects provide for methods of treating a bacterial infection comprising administering to subject in need thereof an amount of the polypeptide effective to treat the infection. Any subject with a bacterial infection can be treated using the methods.

As used herein, "treating a bacterial infection" means accomplishing one or more of the following: (a) reducing or eliminating infection in the subject; (b) reducing the severity of one or more symptoms of bacterial infection; (c) limiting or preventing development of one or more symptoms of bacterial infection; (d) inhibiting worsening of one or more symptom of bacterial infection; and (e) limiting or preventing recurrence of one or more symptoms of bacterial infection in subjects that were previously symptomatic for the relevant symptom.

The invention claimed is:

1. A method of treating bacterial infection or allergen induced rhinitis or allergen induced asthma comprising administering to a subject having a bacterial infection of the lungs or allergen induced rhinitis or allergen induced asthma a NEIL2 polypeptide comprising an amino acid sequence having at least 90% amino acid sequence identity to the amino acid sequence of SEQ ID NO: 1 non-covalently coupled to a lung targeting moiety,the lung targeting moiety localizing the NEIL2 polypeptide in the cytosol or nucleus of the targeted cell, wherein damage to transcribed genomic DNA in the lung is reduced relative to a subject not treated with said NEIL2 polypeptide, thereby ameliorating the negative effect of bacterial infection of the lung on an innate immune response in the subject.

2. The method of claim 1, wherein the lung targeting moiety is a peptide consisting of the amino acid sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14.

3. The method of claim 1, wherein the NEIL2 polypeptide comprises the amino acid sequence of SEQ ID NO: 1.

4. The method of claim 1, wherein the NEIL2 polypeptide complex is administered to the lungs by inhalation or instillation.

5. The method of claim 1, wherein the NEIL2 polypeptide complex is administered intranasally.

6. The method of claim 1, wherein the bacterial infection is a *Klebsiella infection*.

7. The method of claim 1, wherein the bacterial infection is an *Acinetobacter* infection.

* * * * *

SEQUENCE LISTING

```
<160> NUMBER OF SEQ ID NOS: 33

<210> SEQ ID NO 1
<211> LENGTH: 332
<212> TYPE: PRT
<213> ORGANISM: Homo sapiens

<400> SEQUENCE: 1

Met Pro Glu Gly Pro Leu Val Arg Lys Phe His His Leu Val Ser Pro
1               5                   10                  15

Phe Val Gly Gln Gln Val Val Lys Thr Gly Gly Ser Ser Lys Lys Leu
                20                  25                  30

Gln Pro Ala Ser Leu Gln Ser Leu Trp Leu Gln Asp Thr Gln Val His
            35                  40                  45

Gly Lys Lys Leu Phe Leu Arg Phe Asp Leu Asp Glu Glu Met Gly Pro
        50                  55                  60

Pro Gly Ser Ser Pro Thr Pro Glu Pro Gln Lys Glu Val Gln Lys
65                  70                  75                  80

Glu Gly Ala Ala Asp Pro Lys Gln Val Gly Glu Pro Ser Gly Gln Lys
                85                  90                  95
```

```
Thr Leu Asp Gly Ser Ser Arg Ser Ala Glu Leu Val Pro Gln Gly Glu
            100                 105                 110

Asp Asp Ser Glu Tyr Leu Glu Arg Asp Ala Pro Ala Gly Asp Ala Gly
        115                 120                 125

Arg Trp Leu Arg Val Ser Phe Gly Leu Phe Gly Ser Val Trp Val Asn
    130                 135                 140

Asp Phe Ser Arg Ala Lys Lys Ala Asn Lys Arg Gly Asp Trp Arg Asp
145                 150                 155                 160

Pro Ser Pro Arg Leu Val Leu His Phe Gly Gly Gly Phe Leu Ala
                165                 170                 175

Phe Tyr Asn Cys Gln Leu Ser Trp Ser Ser Pro Val Thr Pro
                180                 185                 190

Thr Cys Asp Ile Leu Ser Glu Lys Phe His Arg Gly Gln Ala Leu Glu
                195                 200                 205

Ala Leu Gly Gln Ala Gln Pro Val Cys Tyr Thr Leu Leu Asp Gln Arg
        210                 215                 220

Tyr Phe Ser Gly Leu Gly Asn Ile Ile Lys Asn Glu Ala Leu Tyr Arg
225                 230                 235                 240

Ala Gly Ile His Pro Leu Ser Leu Gly Ser Val Leu Ser Ala Ser Arg
                245                 250                 255

Arg Glu Val Leu Val Asp His Val Val Glu Phe Ser Thr Ala Trp Leu
                260                 265                 270

Gln Gly Lys Phe Gln Gly Arg Pro Gln His Thr Gln Val Tyr Gln Lys
            275                 280                 285

Glu Gln Cys Pro Ala Gly His Gln Val Met Lys Glu Ala Phe Gly Pro
        290                 295                 300

Glu Asp Gly Leu Gln Arg Leu Thr Trp Trp Cys Pro Gln Cys Gln Pro
305                 310                 315                 320

Gln Leu Ser Glu Glu Pro Glu Gln Cys Gln Phe Ser
                325                 330

<210> SEQ ID NO 2
<211> LENGTH: 49
<212> TYPE: PRT
<213> ORGANISM: Artificial Sequence
<220> FEATURE:
<223> OTHER INFORMATION: synthetic peptide

<400> SEQUENCE: 2

Lys Lys Lys Lys Ala Ala Val Ala Leu Leu Pro Ala Val Leu Leu Ala
1               5                   10                  15

Leu Leu Ala Pro Met Ser Val Leu Thr Pro Leu Leu Leu Arg Gly Leu
            20                  25                  30

Thr Gly Ser Ala Arg Arg Leu Pro Val Pro Arg Ala Lys Ile His Ser
        35                  40                  45

Leu

<210> SEQ ID NO 3
<211> LENGTH: 53
<212> TYPE: PRT
<213> ORGANISM: Artificial Sequence
<220> FEATURE:
<223> OTHER INFORMATION: synthetic peptide

<400> SEQUENCE: 3

Lys Lys Lys Lys Lys Lys Lys Lys Ala Ala Val Ala Leu Leu Pro Ala
1               5                   10                  15
```

```
Val Leu Leu Ala Leu Leu Ala Pro Met Ser Val Leu Thr Pro Leu Leu
             20                  25                  30

Leu Arg Gly Leu Thr Gly Ser Ala Arg Arg Leu Pro Val Pro Arg Ala
         35                  40                  45

Lys Ile His Ser Leu
        50
```

<210> SEQ ID NO 4
<211> LENGTH: 57
<212> TYPE: PRT
<213> ORGANISM: Artificial Sequence
<220> FEATURE:
<223> OTHER INFORMATION: synthetic peptide

<400> SEQUENCE: 4

```
Lys Lys Lys Lys Lys Lys Lys Lys Lys Lys Lys Lys Ala Ala Val Ala
1               5                   10                  15

Leu Leu Pro Ala Val Leu Leu Ala Leu Leu Ala Pro Met Ser Val Leu
             20                  25                  30

Thr Pro Leu Leu Leu Arg Gly Leu Thr Gly Ser Ala Arg Arg Leu Pro
         35                  40                  45

Val Pro Arg Ala Lys Ile His Ser Leu
        50                  55
```

<210> SEQ ID NO 5
<211> LENGTH: 61
<212> TYPE: PRT
<213> ORGANISM: Artificial Sequence
<220> FEATURE:
<223> OTHER INFORMATION: synthetic peptide

<400> SEQUENCE: 5

```
Lys Lys Lys Lys Lys Lys Lys Lys Lys Lys Lys Lys Lys Lys Lys Lys
1               5                   10                  15

Ala Ala Val Ala Leu Leu Pro Ala Val Leu Leu Ala Leu Leu Ala Pro
             20                  25                  30

Met Ser Val Leu Thr Pro Leu Leu Leu Arg Gly Leu Thr Gly Ser Ala
         35                  40                  45

Arg Arg Leu Pro Val Pro Arg Ala Lys Ile His Ser Leu
        50                  55                  60
```

<210> SEQ ID NO 6
<211> LENGTH: 20
<212> TYPE: PRT
<213> ORGANISM: Artificial Sequence
<220> FEATURE:
<223> OTHER INFORMATION: synthetic peptide

<400> SEQUENCE: 6

```
Lys Lys Lys Lys Ala Ala Val Ala Leu Leu Pro Ala Val Leu Leu Ala
1               5                   10                  15

Leu Leu Ala Pro
             20
```

<210> SEQ ID NO 7
<211> LENGTH: 24
<212> TYPE: PRT
<213> ORGANISM: Artificial Sequence
<220> FEATURE:
<223> OTHER INFORMATION: synthetic peptide

<400> SEQUENCE: 7

-continued

Lys Lys Lys Lys Lys Lys Lys Ala Ala Val Ala Leu Leu Pro Ala
1               5                   10                  15

Val Leu Leu Ala Leu Leu Ala Pro
            20

<210> SEQ ID NO 8
<211> LENGTH: 28
<212> TYPE: PRT
<213> ORGANISM: Artificial Sequence
<220> FEATURE:
<223> OTHER INFORMATION: synthetic peptide

<400> SEQUENCE: 8

Lys Lys Lys Lys Lys Lys Lys Lys Lys Lys Lys Ala Ala Val Ala
1               5                   10                  15

Leu Leu Pro Ala Val Leu Leu Ala Leu Leu Ala Pro
            20                  25

<210> SEQ ID NO 9
<211> LENGTH: 32
<212> TYPE: PRT
<213> ORGANISM: Artificial Sequence
<220> FEATURE:
<223> OTHER INFORMATION: synthetic peptide

<400> SEQUENCE: 9

Lys Lys Lys Lys Lys Lys Lys Lys Lys Lys Lys Lys Lys Lys Lys
1               5                   10                  15

Ala Ala Val Ala Leu Leu Pro Ala Val Leu Leu Ala Leu Leu Ala Pro
            20                  25                  30

<210> SEQ ID NO 10
<211> LENGTH: 33
<212> TYPE: PRT
<213> ORGANISM: Artificial Sequence
<220> FEATURE:
<223> OTHER INFORMATION: synthetic peptide

<400> SEQUENCE: 10

Tyr Lys Lys Lys Lys Lys Lys Lys Lys Lys Lys Lys Lys Lys Lys
1               5                   10                  15

Lys Ala Ala Val Ala Leu Leu Pro Ala Val Leu Leu Ala Leu Leu Ala
            20                  25                  30

Pro

<210> SEQ ID NO 11
<211> LENGTH: 48
<212> TYPE: PRT
<213> ORGANISM: Artificial Sequence
<220> FEATURE:
<223> OTHER INFORMATION: synthetic peptide

<400> SEQUENCE: 11

Lys Lys Lys Lys Lys Lys Lys Lys Lys Lys Lys Lys Lys Lys Lys
1               5                   10                  15

Ala Ala Val Ala Leu Leu Pro Ala Val Leu Leu Ala Leu Leu Ala Pro
            20                  25                  30

Ala Ala Val Ala Leu Leu Pro Ala Val Leu Leu Ala Leu Leu Ala Pro
            35                  40                  45

<210> SEQ ID NO 12
<211> LENGTH: 44
<212> TYPE: PRT

```
<213> ORGANISM: Artificial Sequence
<220> FEATURE:
<223> OTHER INFORMATION: synthetic peptide

<400> SEQUENCE: 12

Ala Ala Val Ala Leu Leu Pro Ala Val Leu Leu Ala Leu Leu Ala Pro
1               5                   10                  15

Lys Lys Lys Lys Lys Lys Lys Lys Lys Lys Lys Ala Ala Val Ala
            20                  25                  30

Leu Leu Pro Ala Val Leu Leu Ala Leu Leu Ala Pro
        35                  40

<210> SEQ ID NO 13
<211> LENGTH: 32
<212> TYPE: PRT
<213> ORGANISM: Artificial Sequence
<220> FEATURE:
<223> OTHER INFORMATION: synthetic peptide

<400> SEQUENCE: 13

Lys Lys Lys Lys Lys Lys Lys Lys Lys Lys Lys Lys Lys Lys Lys Lys
1               5                   10                  15

Ala Ala Val Trp Leu Leu Trp Tyr Val Leu Leu Phe Leu Leu Tyr Leu
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: synthetic peptide

<400> SEQUENCE: 14

Lys Lys Lys Lys Lys Lys Lys Lys Lys Lys Lys Lys Lys Lys Lys Lys
1               5                   10                  15

Phe Trp Val Trp Leu Leu Trp Tyr Val Leu Leu Phe Leu Leu Tyr Leu
            20                  25                  30

<210> SEQ ID NO 15
<211> LENGTH: 4
<212> TYPE: PRT
<213> ORGANISM: Artificial Sequence
<220> FEATURE:
<223> OTHER INFORMATION: synthetic peptide

<400> SEQUENCE: 15

Lys Lys Lys Lys
1

<210> SEQ ID NO 16
<211> LENGTH: 8
<212> TYPE: PRT
<213> ORGANISM: Artificial Sequence
<220> FEATURE:
<223> OTHER INFORMATION: synthetic peptide

<400> SEQUENCE: 16

Lys Lys Lys Lys Lys Lys Lys Lys
1               5

<210> SEQ ID NO 17
<211> LENGTH: 12
<212> TYPE: PRT
<213> ORGANISM: Artificial Sequence
<220> FEATURE:
```

```
<223> OTHER INFORMATION: synthetic peptide

<400> SEQUENCE: 17

Lys Lys Lys Lys Lys Lys Lys Lys Lys Lys Lys Lys
1               5                   10

<210> SEQ ID NO 18
<211> LENGTH: 16
<212> TYPE: PRT
<213> ORGANISM: Artificial Sequence
<220> FEATURE:
<223> OTHER INFORMATION: synthetic peptide

<400> SEQUENCE: 18

Lys Lys Lys Lys Lys Lys Lys Lys Lys Lys Lys Lys Lys Lys Lys Lys
1               5                   10                  15

<210> SEQ ID NO 19
<211> LENGTH: 4
<212> TYPE: PRT
<213> ORGANISM: Artificial Sequence
<220> FEATURE:
<223> OTHER INFORMATION: synthetic peptide

<400> SEQUENCE: 19

Arg Arg Arg Arg
1

<210> SEQ ID NO 20
<211> LENGTH: 8
<212> TYPE: PRT
<213> ORGANISM: Artificial Sequence
<220> FEATURE:
<223> OTHER INFORMATION: synthetic peptide

<400> SEQUENCE: 20

Arg Arg Arg Arg Arg Arg Arg Arg
1               5

<210> SEQ ID NO 21
<211> LENGTH: 12
<212> TYPE: PRT
<213> ORGANISM: Artificial Sequence
<220> FEATURE:
<223> OTHER INFORMATION: synthetic peptide

<400> SEQUENCE: 21

Arg Arg Arg Arg Arg Arg Arg Arg Arg Arg Arg Arg
1               5                   10

<210> SEQ ID NO 22
<211> LENGTH: 16
<212> TYPE: PRT
<213> ORGANISM: Artificial Sequence
<220> FEATURE:
<223> OTHER INFORMATION: synthetic peptide

<400> SEQUENCE: 22

Arg Arg Arg Arg Arg Arg Arg Arg Arg Arg Arg Arg Arg Arg Arg Arg
1               5                   10                  15

<210> SEQ ID NO 23
<211> LENGTH: 4
<212> TYPE: PRT
<213> ORGANISM: Artificial Sequence
<220> FEATURE:
<223> OTHER INFORMATION: synthetic peptide
```

```
<400> SEQUENCE: 23

Lys Arg Lys Arg
1

<210> SEQ ID NO 24
<211> LENGTH: 4
<212> TYPE: PRT
<213> ORGANISM: Artificial Sequence
<220> FEATURE:
<223> OTHER INFORMATION: synthetic peptide

<400> SEQUENCE: 24

Lys Lys Lys Arg
1

<210> SEQ ID NO 25
<211> LENGTH: 12
<212> TYPE: PRT
<213> ORGANISM: Artificial Sequence
<220> FEATURE:
<223> OTHER INFORMATION: synthetic peptide

<400> SEQUENCE: 25

Lys Lys Lys Arg Arg Arg Lys Lys Lys Arg Arg Arg
1               5                   10

<210> SEQ ID NO 26
<211> LENGTH: 16
<212> TYPE: PRT
<213> ORGANISM: Artificial Sequence
<220> FEATURE:
<223> OTHER INFORMATION: synthetic peptide

<400> SEQUENCE: 26

Lys Lys Lys Lys Arg Arg Arg Arg Lys Lys Lys Lys Arg Arg Arg Arg
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (1)..(1)
<223> OTHER INFORMATION: X = V, I, L, M, F, W, C, A, Y, H, T, S, P, or G
<220> FEATURE:
<221> NAME/KEY: PEPTIDE
<222> LOCATION: (3)..(3)
<223> OTHER INFORMATION: X = V, I, L, M, F, W, C, A, Y, H, T, S, P, or G
<220> FEATURE:
<221> NAME/KEY: PEPTIDE
<222> LOCATION: (7)..(7)
<223> OTHER INFORMATION: X = V, I, L, M, F, W, C, A, Y, H, T, S, P, or G

<400> SEQUENCE: 27

Xaa Arg Xaa Leu Arg Arg Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic peptide

<400> SEQUENCE: 28
```

```
Pro Lys Lys Lys Arg Lys Val
1               5

<210> SEQ ID NO 29
<211> LENGTH: 25
<212> TYPE: PRT
<213> ORGANISM: Artificial Sequence
<220> FEATURE:
<223> OTHER INFORMATION: synthetic peptide

<400> SEQUENCE: 29

Leu Val Arg Lys Lys Arg Lys Thr Glu Glu Ser Pro Leu Lys Asp
1               5                   10                  15

Lys Asp Ala Lys Lys Ser Lys Gln Glu
            20                  25

<210> SEQ ID NO 30
<211> LENGTH: 12
<212> TYPE: PRT
<213> ORGANISM: Artificial Sequence
<220> FEATURE:
<223> OTHER INFORMATION: synthetic peptide

<400> SEQUENCE: 30

Pro Glu Val Lys Lys Lys Arg Lys Pro Glu Tyr Pro
1               5                   10

<210> SEQ ID NO 31
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: X = L, A, W, F, Y, or V
<220> FEATURE:
<221> NAME/KEY: VARIANT
<222> LOCATION: (2)..(2)
<223> OTHER INFORMATION: X = L, A, W, F, Y, or V
<220> FEATURE:
<221> NAME/KEY: VARIANT
<222> LOCATION: (4)..(4)
<223> OTHER INFORMATION: X = L, A, W, F, Y, or V
<220> FEATURE:
<221> NAME/KEY: VARIANT
<222> LOCATION: (7)..(7)
<223> OTHER INFORMATION: X = L, A, W, F, Y, or V
<220> FEATURE:
<221> NAME/KEY: VARIANT
<222> LOCATION: (8)..(8)
<223> OTHER INFORMATION: X = L, A, W, F, Y, or V
<220> FEATURE:
<221> NAME/KEY: VARIANT
<222> LOCATION: (12)..(12)
<223> OTHER INFORMATION: X = L, A, W, F, Y, or V
<220> FEATURE:
<221> NAME/KEY: VARIANT
<222> LOCATION: (15)..(15)
<223> OTHER INFORMATION: X = L, A, W, F, Y, or V
<220> FEATURE:
<221> NAME/KEY: VARIANT
<222> LOCATION: (16)..(16)
<223> OTHER INFORMATION: X = L, A, W, F, Y, or V

<400> SEQUENCE: 31

Xaa Xaa Val Xaa Leu Leu Xaa Xaa Val Leu Leu Xaa Leu Leu Xaa Xaa
1               5                   10                  15
```

-continued

```
<210> SEQ ID NO 32
<211> LENGTH: 16
<212> TYPE: PRT
<213> ORGANISM: Artificial Sequence
<220> FEATURE:
<223> OTHER INFORMATION: sytnhetic peptide

<400> SEQUENCE: 32

Ala Ala Val Ala Leu Leu Pro Ala Val Leu Leu Ala Leu Leu Ala Pro
1               5                   10                  15

<210> SEQ ID NO 33
<211> LENGTH: 45
<212> TYPE: PRT
<213> ORGANISM: Artificial Sequence
<220> FEATURE:
<223> OTHER INFORMATION: synthetic peptide

<400> SEQUENCE: 33

Ala Ala Val Ala Leu Leu Pro Ala Val Leu Leu Ala Leu Leu Ala Pro
1               5                   10                  15

Met Ser Val Leu Thr Pro Leu Leu Leu Arg Gly Leu Thr Gly Ser Ala
            20                  25                  30

Arg Arg Leu Pro Val Pro Arg Ala Lys Ile His Ser Leu
        35                  40                  45
```